United States Patent [19]
Nelson et al.

[11] Patent Number: 6,007,690
[45] Date of Patent: *Dec. 28, 1999

[54] INTEGRATED MICROFLUIDIC DEVICES

[75] Inventors: Robert J. Nelson, Alameda; Herbert H. Hooper, Belmont; Alan K. Hauser, Palo Alto; Alexander P. Sassi, Berkeley, all of Calif.

[73] Assignee: Aclara Biosciences, Inc., Hayward, Calif.

[*] Notice: This patent is subject to a terminal disclaimer.

[21] Appl. No.: 08/902,855

[22] Filed: Jul. 30, 1997

Related U.S. Application Data

[63] Continuation-in-part of application No. 08/690,307, Jul. 30, 1996, Pat. No. 5,770,029.

[51] Int. Cl.$^6$ .......................... G01N 27/26; G01N 27/447
[52] U.S. Cl. .......................... 204/601; 204/450; 204/451; 204/600
[58] Field of Search .................... 204/450, 451, 204/452, 453, 454, 455, 600, 601, 602, 603, 604, 605

[56] References Cited

U.S. PATENT DOCUMENTS

| | | | |
|---|---|---|---|
| 4,714,680 | 12/1987 | Civin | 435/347 |
| 4,908,112 | 3/1990 | Pace | 204/601 X |
| 4,931,328 | 6/1990 | Swedberg | 204/601 |
| 5,006,313 | 4/1991 | Swedberg | 422/70 X |
| 5,081,030 | 1/1992 | Civin | 435/380 |
| 5,085,756 | 2/1992 | Swedberg | 204/605 |
| 5,110,514 | 5/1992 | Soane | 264/496 |
| 5,110,745 | 3/1994 | Kricka et al. | 436/87 |
| 5,114,768 | 5/1992 | Swedberg | 204/601 X |
| 5,126,022 | 6/1992 | Soane et al. | 204/458 |
| 5,132,012 | 7/1992 | Miura et al. | 210/198.2 |
| 5,180,480 | 1/1993 | Manz | 204/644 |
| 5,202,010 | 4/1993 | Guzman | 204/601 |
| 5,246,577 | 9/1993 | Fuchs et al. | 204/604 |

(List continued on next page.)

FOREIGN PATENT DOCUMENTS

| | | |
|---|---|---|
| 637 996 B1 | 4/1993 | European Pat. Off. . |
| 637 997 B1 | 4/1993 | European Pat. Off. . |
| 637 998 B1 | 4/1993 | European Pat. Off. . |
| 0 815 940 A2 | 1/1998 | European Pat. Off. . |
| 0 816 837 A1 | 1/1998 | European Pat. Off. . |

(List continued on next page.)

OTHER PUBLICATIONS

Tomlinson et al., "Improved On–Line Membrane Preconcentration–Capillary Electrophoresis (mPC–CE), " J. High Res. Chrom. (1995) 18:381–3.

Barron & Blanch, "DNA Separations by Slab Gel and Capillary Electrophoresis: Theory and Practice," Separation and Purification Methods (1995) 24:1–118.

K. Hofmann et al., "Avidin Binding of Carboxyl–Substituted Biotin and Analolgues," (1982), Biochemistry vol. 21, pp. 978–984.

Simpson et al., "Microfabricated Capillary Array Electrophoresis Device and Method," 1997.

(List continued on next page.)

*Primary Examiner*—Jill Warden
*Assistant Examiner*—John S. Starsiak, Jr.
*Attorney, Agent, or Firm*—Bertram Rowland; Rae-Venter Law Group, P.C.

[57] ABSTRACT

Integrated microfluidic devices comprising at least an enrichment channel and a main electrophoretic flowpath are provided. In the subject integrated devices, the enrichment channel and the main electrophoretic flowpath are positioned so that waste fluid flows away from said main electrophoretic flowpath through a discharge outlet. The subject devices find use in a variety of electrophoretic applications, including clinical assays, high throughput screening for genomics and pharmaceutical applications, point-or-care in vitro diagnostics, molecular genetic analysis and nucleic acid diagnostics, cell separations, and bioresearch generally.

36 Claims, 14 Drawing Sheets

U.S. PATENT DOCUMENTS

| | | | |
|---|---|---|---|
| 5,294,534 | 3/1994 | Dattagupta et al. | 435/6 |
| 5,296,114 | 3/1994 | Manz | 204/451 |
| 5,296,375 | 3/1994 | Kricka et al. | 435/2 |
| 5,304,487 | 4/1994 | Wilding et al. | 435/29 |
| 5,318,680 | 6/1994 | Fishman et al. | 204/453 |
| 5,340,452 | 8/1994 | Brenner et al. | 204/453 |
| 5,423,966 | 6/1995 | Wiktorowicz | 204/453 |
| 5,427,946 | 6/1995 | Kricka et al. | 435/288.5 |
| 5,486,335 | 1/1996 | Wilding et al. | 422/55 X |
| 5,498,392 | 3/1996 | Wilding et al. | 422/68.1 |
| 5,500,071 | 3/1996 | Kaltenbach et al. | 156/272.8 |
| 5,514,340 | 5/1996 | Lansdrop et al. | 422/101 |
| 5,571,410 | 11/1996 | Swedberg et al. | 210/198.2 |
| 5,585,069 | 12/1996 | Zanzucchi et al. | 422/100 |
| 5,587,128 | 12/1996 | Wilding et al. | 422/50 |
| 5,593,838 | 1/1997 | Zanzucchi et al. | 435/6 |
| 5,599,432 | 2/1997 | Manz et al. | 204/601 X |
| 5,603,351 | 2/1997 | Cherukuri et al. | 137/597 |
| 5,632,876 | 5/1997 | Zanzucchi et al. | 204/600 |
| 5,635,358 | 6/1997 | Wilding et al. | 435/7.2 |
| 5,637,469 | 6/1997 | Wilding et al. | 435/7.21 |
| 5,641,400 | 6/1997 | Kaltenbach et al. | 210/198.2 |
| 5,643,738 | 7/1997 | Zanzucchi et al. | 435/6 |
| 5,645,702 | 7/1997 | Witt et al. | 204/501 |
| 5,646,001 | 7/1997 | Terstrappen et al. | 435/7.21 |
| 5,646,048 | 7/1997 | Templin et al. | 436/180 |
| 5,658,413 | 8/1997 | Kaltenbach et al. | 156/272.8 |
| 5,681,484 | 10/1997 | Zanzucchi et al. | 216/2 |
| 5,691,208 | 11/1997 | Miltenyi et al. | 436/526 |
| 5,699,157 | 12/1997 | Parce | 356/344 |
| 5,726,026 | 3/1998 | Wilding et al. | 435/7.21 |
| 5,744,366 | 4/1998 | Kricka et al. | 436/63 |
| 5,747,169 | 5/1998 | Fan et al. | 428/426 |
| 5,755,942 | 5/1998 | Zanzucchi et al. | 204/454 |
| 5,824,481 | 10/1998 | Kambara et al. | 435/6 |

FOREIGN PATENT DOCUMENTS

| | | |
|---|---|---|
| 5-164737 | 6/1993 | Japan. |
| WO 93/05390 | 3/1993 | WIPO. |
| WO96/15450 | 11/1995 | WIPO. |
| WO96/15576 | 11/1995 | WIPO. |
| WO96/39252 | 11/1995 | WIPO. |
| WO96/39260 | 11/1995 | WIPO. |
| WO 96/31776 | 10/1996 | WIPO. |
| WO97/16561 | 11/1996 | WIPO. |
| WO97/16835 | 11/1996 | WIPO. |
| WO97/27324 | 1/1997 | WIPO. |
| WO97/37755 | 4/1997 | WIPO. |
| WO97/43629 | 5/1997 | WIPO. |
| WO98/13683 | 9/1997 | WIPO. |
| WO 98/00231 | 1/1998 | WIPO. |
| WO 98/00705 | 1/1998 | WIPO. |
| WO 98/00707 | 1/1998 | WIPO. |

OTHER PUBLICATIONS

Wooley et al., "Ultra–high–speed DNA fragment separations using Microfabricated capillary array electrophoresis chips," *PNAS USA,* (1994), vol. 91, pp. 11348–11352.

Guzman, "Biomedical applications of on–line preconcentration–capillary electrophoresis using an analyte concentrator:; investigation of design options," *J Liquid Chro* 1995), pp. 3751–3768.

Cole et al., "Selective preconcentration for capillary zone electrophoresis using protein G immunoaffinity capillary chromatography," *Electrophoresis* (1995), pp. 549–556.

Cai et al., "Selective On–Line Preconcentration of Proteins by Tandem Metal Chelate Capillaries–Capillary Zone Electrophoresis," *J. Liquid Chro* (1993), pp. 2007–2004.

Cai et al., "On–Line Preconcentration of Triazine Herbicides with Tandem Octadecyl Capillaries–Capillary Zone Electrophoresis," *J Liquid Chrom* (1992), pp. 1179–1192.

Kasicka et al., "Isotachophoretic Electrodesorption of Proteins From an Affinity Adsorbent on a Microscale," *J. Chrom* (1983), PGS 117–128.

Stegehuis et al., "Isotachophoresis as an on–line concentration pretreatment technique in capillary electrophoresis," *J. Chrom* (1991), pp. 393–402.

Chien et al., "Field amplified sample injection in high–performance capillary electrophoresis," *J. Chrom* (1991), pp. 141–152.

Beckers et al., "Effect of sample stacking on resolution, calbration graphs and pH in capillary zone electrophoresis," *J. Chrom.* (1993), pp. 371–378.

Effenhauser et al., "High–Speed Separation of Antisense Oligonucleotides on a Micromachined Capillary Electrophoresis Device," *Anal. Chem* (1994), pp. 2949–2953.

Jacobson et al., "Precolumn Reactions with Electrophoretic Analysis Integrated on a Microchip," *Anal Chem.* (1994), pp. 4127–4132.

Harrison et al., "Micromachining a Miniaturized Capillary Electrophoresis–Based Chemical Analysis System on a chip," *Sciences* (1993), vol. 261, pp. 895–897.

Tomlinson et al., "Enhancement of Concentration limits of detection in CE and CE–MS: A review of on–line sample extraction, clean–up, analyte preconcentration, and microreactor technology," *J Cap Ele* (1995) pp. 247–266.

INTEGRATED MICROFLUIDIC DEVICES

This application is a Continuation-in-Part of U.S. Ser. No. 08/690,307, filed Jul. 30, 1996, now U.S. Pat. No. 5,770,029.

BACKGROUND

This invention relates to microfluidics, and particularly to microchannel devices in which fluids are manipulated at least in part by application of electrical fields.

Electrophoresis has become an indispensable tool of the biotechnology and other industries, as it is used extensively in a variety of applications, including the separation, identification and preparation of pure samples of nucleic acids, proteins, carbohydrates, the identification of a particular analyte in a complex mixture, and the like. Of increasing interest in the broader field of electrophoresis is capillary electrophoresis (CE), where particular entities or species are moved through a medium in an electrophoretic chamber of capillary dimensions under the influence of an applied electric field. Benefits of CE include rapid run times, high separation efficiency, small sample volumes, etc. Although CE was originally carried out in capillary tubes, of increasing interest is the practice of using microchannels or trenches of capillary dimension on a planar substrate, known as microchannel electrophoresis (MCE). CE and MCE are increasingly finding use in a number of different applications in both basic research and industrial processes, including analytical, biomedical, pharmaceutical, environmental, molecular, biological, food and clinical applications.

Despite the many advantages of CE and MCE, the potential benefits of these techniques have not yet been fully realized for a variety of reasons. Because of the nature of the electrophoretic chambers employed in CE and MCE, good results are not generally obtainable with samples having analyte concentrations of less than about $10^{-6}$ M. This lower analyte concentration detection limit has significantly limited the potential applications for CE and MCE. For example, CE and MCE have not found widespread use in clinical applications, where often an analyte of interest is present in femtomolar to nanomolar concentration in a complex sample, such as blood or urine.

In order to improve the detection limits of CE, different techniques have been developed, including improved sample injection procedures, such as analyte stacking (Beckers & Ackermans, "The Effect of Sample Stacking for High Performance Capillary Electrophoresis," J. Chromatogr. (1993) 629: 371–378), field amplification (Chien & Burgi, "Field Amplified Sample Injection in High-Performance Capillary Electrophoresis," J. Chromatogr. (1991) 559: 141–152), and transient isotachophoresis (Stegehuis et al., "Isotachophoresis as an On-Line Concentration Pretreatment Technique in Capillary Electrophoresis," J. Chromatogr. (1991) 538: 393–402), as well as improved sample detection procedures and "off-line" sample preparation procedures.

Another technique that has been developed to improve the detection limit achievable with CE has been to employ an analyte preconcentration device that is positioned directly upstream from the capillary, i.e., in an "on-line" or "single flow path" relationship. As used herein, the term "on-line" and "single flow path" are used to refer to the relationship where all of the fluid introduced into the analyte preconcentration component, i.e., the enriched fraction and the remaining waste fraction of the original sample volume, necessarily flows through the main electrophoretic portion of the device, i.e., the capillary tube comprising the separation medium. A review of the various configurations that have been employed is provided in Tomlinson et al., "Enhancement of Concentration Limits of Detection in CE and CE-MS: A Review of On-Line Sample Extraction, Cleanup, Analyte Preconcentration, and Microreactor Technology," J. Cap. Elec. (1995) 2: 247–266, and the figures provided therein.

Although this latter approach can provide improved results with regard to analyte detection limits, particularly with respect to the concentration limit of detection, it can have a deleterious impact on other aspects of CE, and thereby reduce the overall achievable performance. For example, analyte peak widths can be broader in on-line or single flow path devices comprising analyte preconcentrators.

Accordingly, there is continued interest in the development of improved CE devices capable of providing good results with samples having low concentrations of analyte, particularly analyte concentrations in the femtomolar to nanomolar range.

MCE devices are disclosed in U.S. Pat. No. 5,126,022; U.S. Pat. No. 5,296,114; U.S. Pat. No. 5,180,480; U.S. Pat. No. 5,132,012; and U.S. Pat. No. 4,908,112. Other references describing MCE devices include Harrison et al., "Micromachining a Miniaturized Capillary Electrophoresis-Based Chemical Analysis System on a Chip," Science (1992) 261: 895; Jacobsen et al., "Precolumn Reactions with Electrophoretic Analysis Integrated on a Microchip," Anal. Chem. (1994) 66: 2949; Effenhauser et al., "High-Speed Separation of Antisense Oligonucleotides on a Micromachined Capillary Electrophoresis Device," Anal. Chem. (1994) 66:2949; and Woolley & Mathies, "Ultra-High-Speed DNA Fragment Separations Using Capillary Array Electrophoresis Chips," P.N.A.S. USA (1994) 91:11348.

Patents disclosing devices and methods for the preconcentration of analyte in a sample "on-line" prior to CE include U.S. Pat. No. 5,202,010; U.S. Pat. No. 5,246,577 and U.S. Pat. No. 5,340,452. A review of various methods of analyte preconcentration employed in CE is provided in Tomlinson et al., "Enhancement of Concentration Limits of Detection in CE and CE-MS: A Review of On-Line Sample Extraction, Cleanup, Analyte Preconcentration, and Microreactor Technology," J. Cap. Elec. (1995) 2: 247–266.

SUMMARY OF THE INVENTION

Integrated electrophoretic microdevices comprising at least an enrichment channel and a main electrophoretic flowpath, as well as methods for their use in electrophoretic applications, are provided. The enrichment channel serves to enrich a particular fraction of a liquid sample for subsequent movement through the main electrophoretic flowpath. In the subject devices, the enrichment channel and electrophoretic flowpath are positioned such that waste fluid from the enrichment channel does not flow through the main electrophoretic flowpath, but instead flows through a discharge outlet. The subject devices find use in a variety of electrophoretic applications, where entities are moved through a medium in response to an applied electric field. The subject devices can be particularly useful in high throughput screening, for genomics and pharmaceutical applications such as gene discovery, drug discovery and development, and clinical development; for point-of-care in vitro diagnostics; for molecular genetic analysis and nucleic acid diagnostics; for cell separations including cell isolation and capture; and for bioresearch generally.

DETAILED DESCRIPTION

Figure 1:
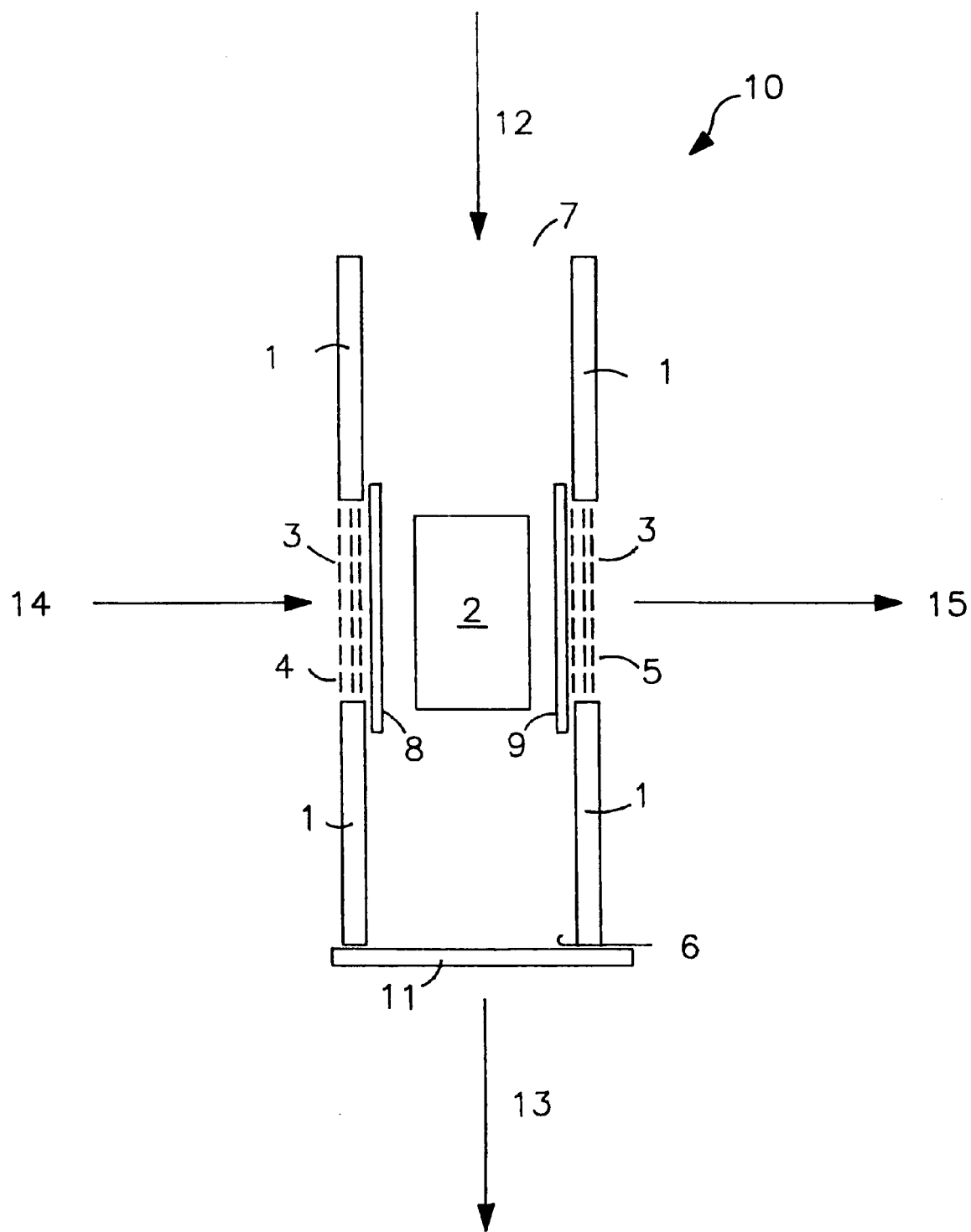
FIG. 1 provides a diagrammatic view of an enrichment channel for use in a device according to the subject invention.

Integrated electrophoretic microdevices comprising at least an enrichment channel and a main electrophoretic flowpath are provided. The enrichment channel serves to enrich a particular analyte comprising fraction of a liquid sample. The enrichment channel and main electrophoretic flowpath are positioned in the device so that waste fluid from the enrichment channel does not flow through the main electrophoretic channel, but instead flows away from the main electrophoretic flowpath through a discharge outlet. The subject devices may be used in a variety of electrophoretic applications, including clinical assay applications. In further describing the invention, the devices will first be described in general terms followed by a discussion of representative specific embodiments of the subject devices with reference to the figures.

The subject device is an integrated electrophoretic microdevice. By integrated is meant that all of the components of the device, e.g., the enrichment channel, the main electrophoretic flowpath, etc., are present in a single, compact, readily handled unit, such as a chip, disk or the like. As the devices are electrophoretic, they are useful in a wide variety of the applications in which entities, such as molecules, particles, cells and the like are moved through a medium under the influence of an applied electric field. Depending on the nature of the entities, e.g., whether or not they carry an electrical charge, as well as the surface chemistry of the electrophoretic chamber in which the electrophoresis is carried out, the entities may be moved through the medium under the direct influence of the applied electric field or as a result of bulk fluid flow through the pathway resulting from the application of the electric field, e.g., electroosmotic flow (EOF). The microdevices will comprise a microchannel as the main electrophoretic flowpath. By microchannel is meant that the electrophoretic chamber of the main electrophoretic flowpath in which the medium is present is a conduit, e.g., trench or channel, having a cross sectional area which provides for capillary flow through the chamber, where the chamber is present on a planar substrate, as will be described below in greater detail.

Critical to the subject device is an enrichment channel that comprises a sample inlet, a waste fluid outlet, an internal enrichment medium for enriching a particular fraction of a sample, and, optionally, an enriched fraction fluid outlet. The purpose of the enrichment channel is to process the initial sample to enrich for a particular fraction thereof, where the particular fraction being enriched comprises the analyte or analytes of interest. The enrichment channel thus serves to selectively retain and separate the target analyte comprising fraction from the remaining components or the waste portion of the initial sample volume. Depending on the particular application in which the device is employed, the enrichment channel can provide for a number of different functions. The enrichment channel can serve to place the analyte of interest into a smaller volume than the initial sample volume, i.e., it can serve as an analyte concentrator. Furthermore, it can serve to prevent potentially interfering sample components from entering and flowing through the main electrophoretic flowpath, i.e., it can serve as a sample "clean-up" means. In addition, the enrichment channel may serve as a microreactor for preparative processes on target analyte present in a fluid sample, such as chemical, immunological, and enzymatic processes, e.g., labeling, protein digestion, DNA digestion or fragmentation, DNA synthesis, and the like.

The enrichment channel may be present in the device in a variety of configurations, depending on the particular enrichment medium housed therein. The internal volume of the channel will usually range from about 1 pl to 1 μl, usually from about 1 pl to 100 nl, where the length of the channel will generally range from about 1 μm to 5 mm, usually 10 μm to 1 mm, and the cross-sectional dimensions (e.g., width, height) will range from about 1 μm to 200 μm, usually from about 10 μm to 100 μm. The cross-sectional shape of the channel may be circular, ellipsoid, rectangular, trapezoidal, square, or other convenient configuration.

A variety of different enrichment media may be present in the enrichment channel. Representative enrichment medium or means include those means described in the analyte preconcentration devices disclosed in U.S. Pat. No. 5,202,010; U.S. Pat. No. 5,246,577 and U.S. Pat. No. 5,340,452, as well as Tomlinson et al., supra, the disclosures of which are herein incorporated by reference. Specific enrichment means known in the art which may be adaptable for use in the subject integrated microchannel electrophoretic devices include: those employed in protein preconcentration devices described in Kasicka & Prusik "Isotachophoretic Electrodesorption of Proteins from an Affinity Adsorbent on a Microscale," J. Chromatogr. (1983) 273:117128; capillary bundles comprising an affinity adsorbent as described in U.S. Pat. No. 5,202,101 and WO 93/05390; octadodecylsilane coated solid phases as described in Cai & El Rassi, "On-Line Preconcentration of Triazine Herbicides with Tandem Octadecyl Capillaries-Capillary Zone Electrophoresis," J. Liq. Chromatogr. (1992) 15:1179–1192; solid phases coated with a metal chelating layer as described in Cai & El Rassi, "Selective On-Line Preconcentration of Proteins by Tandem Metal Chelate Capillaries-Capillary Zone Electrophoresis," J. Liq. Chromatogr. (1993) 16:2007–2024; reversed-phase HPLC solid packing materials as described in U.S. Pat. No. 5,246,577), Protein G coated solid phases as described in Cole & Kennedy, "Selective Preconcentration for Capillary Zone Electrophoresis Using Protein G Immunoaffinity Capillary Chromatography," Electrophoresis (1995) 16:549–556; meltable agarose gels as described in U.S. Pat. No. 5,423,966; affinity adsorbent materials as described in Guzman, "Biomedical Applications of On-Line Preconcentration—Capillary Electrophoresis Using an Analyte Concentrator: Investigation of Design Options," J. Liq. Chromatogr. (1995) 18:3751–3568); and solid phase reactor materials as described in U.S. Pat. No. 5,318,680. The disclosures of each of the above-referenced patents and other publications are hereby incorporated by reference herein.

One class of enrichment media or materials that may find use as enrichment media are chromatographic media or materials, particularly sorptive phase materials. Such materials include: reverse phase materials, e.g., C8 or C18 compound coated particles; ion-exchange materials; affinity chromatographic materials in which a binding member is covalently bound to an insoluble matrix, where the binding member may group specific, e.g., a lectin, enzyme cofactor, Protein A and the like, or substance specific, e.g., antibody or binding fragment thereof, antigen for a particular antibody of interest, oligonucleotide and the like, where the insoluble matrix to which the binding member is bound may be particles, such as porous glass, polymeric beads, magnetic beads, networks of glass strands or filaments, a plurality of narrow rods or capillaries, the wall of the channel and the like. Depending on the nature of the chromatographic material employed as the enrichment means, it may be necessary to employ a retention means to keep the chromatographic material in the enrichment channel. Conveniently, glass frits or plugs of agarose gel may be employed to cover the fluid outlets or inlets of the chamber, where the frits or plugs allow for fluid flow but not for particle or other insoluble matrix flow out of the enrichment channel. In embodiments where the enrichment means is a chromatographic material, typically sample will be introduced into, and allowed to flow through, the enrichment channel. As the sample flows through the enrichment channel, the analyte comprising fraction will be retained in the enrichment channel by the chromatographic material and the remaining waste portion of the sample will flow out of the channel through the waste outlet.

In embodiments where the enrichment means is a bed of polymeric beads or paramagnetic beads or particles, the beads may be coated with antibodies or other target-specific affinity binding moiety, including: affinity purified monoclonal antibodies to any of a variety of mammalian cell markers, particularly human cell markers, including markers for T cells, T cell subsets, B cells, monocytes, stem cells, myeloid cells, leukocytes, and HLA Class II positive cells; secondary antibodies to any of a variety of rodent cell markers, particularly mouse, rat or rabbit immunoglobulins, for isolation of B cells, T cells, and T cell subsets; uncoated or tosylactivated form for custom coating with any given biomolecule; and streptavidin-coated for use with biotinylated antibodies. Paramagnetic beads or particles may be retained in the enrichment channel by application of a magnetic field.

Alternatively, or in addition to solid phase materials such as coated particles or other insoluble matrices as the enrichment means, one may employ a coated and/or impregnated membrane which provides for selective retention of the analyte comprising fraction of the sample while allowing the remainder of the sample to flow through the membrane and out of the enrichment means through the waste outlet. A variety of hydrophilic, hydrophobic and ion-exchange membranes have been developed for use in solid phase extraction which may find use in the subject invention. See, for example, Tomlinson et al., "Novel Modifications and Clinical Applications of Preconcentration-Capillary Electrophoresis-Mass Spectrometry," J. Cap. Elect. (1995) 2: 97–104; and Tomlinson et al., "Improved On-line Membrane Preconcentration-Capillary Electrophoresis (mPC-CE),"J. High Res. Chromatogr. (1995) 18:381–3.

Alternatively or additionally, the enrichment channel or the enrichment medium can include a porous membrane or filter. Suitable materials for capturing genomic DNAs and viral nucleic acids include those marketed by QIAGEN under the name QIAmp, for analysis of blood, tissues, and viral RNAs; and suitable materials for capturing DNAs from plant cells and tissues include those marketed by QIAGEN under the name DNeasy.

Depending on the configuration of the device, the sample can be caused to flow through the enrichment channel by any of a number of different means, and combinations of means. In some device configurations, it may be sufficient to allow the sample to flow through the device as a result of gravity forces on the sample; in some configurations, the device may be spun about a selected axis to impose a centrfuigal force in a desired direction. In other embodiments, active pumping means may be employed to move sample through the enrichment channel and enrichment means housed therein. In other embodiments, magnetic forces may be applied to move the sample or to capture or immobilize a paramagnetic bead-target complex during wash and elution steps. In yet other embodiments of the subject invention, electrodes may be employed to apply an electric field which causes fluid to move through the enrichment channel. An elution liquid will then be caused to flow through the enrichment medium to release the enriched sample fraction from the material and carry it to the main electrophoretic flowpath. Generally, an applied electric field will be employed to move the elution liquid through the enrichment channel.

Electrophoretic gel media may also be employed as enrichment means in the subject applications. Gel media providing for a diversity of different sieving capabilities are known. By varying the pore size of the media, employing two or more gel media of different porosity, and/or providing for a pore size gradient and selecting the appropriate relationship between the enrichment channel and the main electrophoretic flowpath, one can ensure that only the analyte comprising fraction of interest of the initial sample enters the main electrophoretic flowpath. For example, one could have a device comprising an enrichment channel that intersects the main electrophoretic channel, where the enrichment channel comprises, in the direction of sample flow, a stacking gel of large porosity and a second gel of fine porosity, where the boundary between the gels occurs in the intersection of the enrichment channel and the main electrophoretic flowpath. In this embodiment, after sample is introduced into the stacking gel and an electric field applied to the gels in the enrichment channel, the sample components move through the stacking gel and condense into a narrow band at the gel interface in the intersection of the enrichment channel and main electrophoretic flowpath. A second electric field can then be applied to the main electrophoretic flowpath so that the narrow band of the enriched sample fraction moves into and through the main electrophoretic flowpath. Alternatively, the enrichment channel could comprise a gel of gradient porosity. In this embodiment, when the band(s) of interest reaches the intersection of the enrichment channel and electrophoretic flowpath, the band(s) of interest can then be moved into and along the main electrophoretic flowpath.

Enrichment media that can be particularly useful for enrichment and/or purification of nucleic acids include sequence specific capture media as well as generic capture media. Generic capture media include, for example: ion exchange and silica resins or membranes which nonspecifically bind nucleic acids, and which can be expected to retain substantially all the DNA in a sample; immobilized single-stranded DNA binding protein (SSB Protein), which can be expected to bind substantially all single-stranded DNA in a sample; poly-dT modified beads, which can be expected to bind substantially all the mRNA in a sample. Sequence specific capture media include beads, membranes or surfaces on which are immobilized any of a variety of capture molecules such as, for example: oligonucleotide probes, which can be expected to bind nucleic acids having complementary sequences in the sample; streptaviden, which can be expected to bind solution phase biotinylated probes which have hybridized with complementary sequences in the sample. Suitable beads for immobilization of capture molecules include chemically or physically crosslinked gels and porous or non-porous resins such as polymeric or silica-based resins.

Suitable capture media for proteins include the following. Suitable capture media for proteins include: ion exchange resins, including anion (e.g., DEAE) and cation exchange; hydrophobic interaction compounds (e.g., C4, C8 and C18 compounds); sulfhydryls; heparins; inherently active surfaces (e.g., plastics, nitrocellulose blotting papers); activated plastic surfaces; aromatic dyes such as Cibacron blue, Remazol orange, and Procion red. For carbohydrate moieties of proteins, lectins, immobilized hydrophobic octyl and phenylalkane derivatives can be suitable. For enzymes, analogs of a specific enzyme substrate-product transition-state intermediate can be suitable; for kinases, calmodulin can be suitable. Suitable capture media for receptors include receptor ligand affinity compounds.

As mentioned above, the enrichment channel will comprise at least one inlet and at least one outlet. Of course, where there is a single inlet, the inlet must serve to admit sample to the enrichment channel at an enrichment phase of the process, and to admit an elution medium during an elution phase of the process. And where there is a single outlet, the outlet must serve to discharge the portion of the sample that has been depleted of the fraction retained by the enrichment media, and to pass to the main electrophoretic microchannel the enriched fraction during the elution phase. Depending on the particular enrichment means housed in the enrichment channel, as well as the particular device configuration, the enrichment channel may have more than one fluid inlet, serving as, e.g., sample inlet and elution buffer inlet; or the enrichment channel may have more than one outlet, serving as, e.g., waste outlet and enriched fraction fluid outlet. Where the enrichment channel is in direct fluid communication with the main electrophoretic channel, i.e., the enrichment channel and main electrophoretic flowpath are joined so that fluid flows from the enrichment channel immediately into the main electrophoretic flowpath, the enrichment channel will comprise, in addition to the waste outlet, an enriched fraction fluid outlet through which the enriched fraction of the sample flows into the main electrophoretic flowpath. When convenient, e.g., for the introduction of wash and/or elution solvent into the enrichment channel, one or more additional fluid inlets may be provided to conduct such solvents into the enrichment channel from fluid reservoirs. To control bulk fluid flow through the enrichment channel, e.g., to prevent waste sample from flowing into the main electrophoretic flowpath, fluid control means, e.g., valves, membranes, etc., may be associated with each of the inlets and outlets. Where desirable for moving fluid and entities through the enrichment channel, e.g., sample, elution buffer, reagents, reactants, wash or rinse solutions, etc., electrodes may be provided capable of applying an electric field to the material and fluid present in the enrichment channel.

The next component of the subject devices is the main electrophoretic flowpath. The main electrophoretic flowpath may have a variety of configurations, including tube-like, trench-like or other convenient configuration, where the cross-sectional shape of the flowpath may be circular, ellipsoid, square, rectangular, triangular and the like so that it forms a microchannel on the surface of the planar substrate in which it is present. The microchannel will have cross-sectional area which provides for capillary fluid flow through the microchannel, where at least one of the cross-sectional dimensions, e.g., width, height, diameter, will be at least about 1 $\mu$m, usually at least about 10 $\mu$m, but will not exceed about 200 $\mu$m, and will usually not exceed about 100 $\mu$m. Depending on the particular nature of the integrated device, the main electrophoretic flowpath may be straight, curved or another convenient configuration on the surface of the planar substrate.

The main electrophoretic flowpath, as well as any additional electrophoretic flowpaths, will have associated with it at least one pair of electrodes for applying an electric field to the medium present in the flowpath. Where a single pair of electrodes is employed, typically one member of the pair will be present at each end of the pathway. Where convenient, a plurality of electrodes may be associated with the electrophoretic flowpath, as described in U.S. Pat. No. 5,126,022, the disclosure of which is herein incorporated by reference, where the plurality of electrodes can provide for precise movement of entities along the electrophoretic flowpath. The electrodes employed in the subject device may be any convenient type capable of applying an appropriate electric field to the medium present in the electrophoretic flowpath with which they are associated.

Critical to the subject invention is that the enrichment channel and the main electrophoretic flowpath are positioned in the device so that substantially only the enriched fraction of the sample flows through the main electrophoretic flowpath. To this end, the device will further comprise a discharge outlet for discharging a portion of sample other than the enriched fraction, e.g., the waste portion, away from the main electrophoretic flowpath. Thus, where the enrichment channel is in direct fluid communication with the main electrophoretic flowpath, the waste fluid flowpath through the enrichment channel will be in an intersecting relationship with the main electrophoretic flowpath. In other embodiments of the subject invention where the enrichment channel and main electrophoretic flowpath are connected by a second electrophoretic flowpath so that they are in indirect fluid communication, the waste flowpath through the enrichment channel does not necessarily have to be in an intersecting relationship with the main electrophoretic flowpath; the waste flowpath and main electrophoretic flowpath could be parallel to one another.

The subject devices will also comprise a means for transferring the enriched fraction from the enrichment channel to the main electrophoretic flowpath. Depending on the particular device configuration, the enriched fraction transfer means can be an enriched fraction fluid outlet, a secondary electrophoretic pathway, or other suitable transfer means. By having a second electrophoretic flowpath in addition to the main electrophoretic flowpath, the possibility exists to employ the second electrophoretic flowpath as a conduit for the enriched sample fraction from the enrichment channel to the main electrophoretic flowpath. In those embodiments where the waste outlet is the sole fluid outlet, the presence of a secondary electrophoretic flowpath will be essential, such that the enrichment channel and the main electrophoretic flowpath are in indirect fluid communication.

In addition to the main and any secondary electrophoretic flowpath serving as an enriched sample transfer means, the subject devices may further comprise one or more additional electrophoretic flowpaths, which may or may not be of capillary dimension and may serve a variety of purposes. With devices comprising a plurality of electrophoretic flowpaths, a variety of configurations are possible, such as a branched configuration in which a plurality of electrophoretic flowpaths are in fluid communication with the main electrophoretic flowpath. See U.S. Pat. No. 5,126,022, the disclosure of which is herein incorporated by reference.

The main electrophoretic flowpath and/or any secondary electrophoretic flowpaths present in the device may optionally comprise, and usually will comprise, fluid reservoirs at one or both termini, i.e., either end, of the flowpaths. Where reservoirs are provided, they may serve a variety of purposes, such as a means for introducing buffer, elution solvent, reagent, rinse and wash solutions, and the like into the main electrophoretic flowpath, receiving waste fluid from the electrophoretic flowpath, and the like.

Another optional component that may be present in the subject devices is a waste fluid reservoir for receiving and storing the waste portion of the initial sample volume from the enrichment channel, where the waste reservoir will be in fluid communication with the discharge outlet. Depending on the particular device configuration, the discharge outlet may be the same as, or distinct from, the waste outlet, and may open into a waste reservoir or provide an outlet from the device. The waste reservoir may be present in the device as a channel, compartment, or other convenient configuration which does not interfere with the other components of the device.

The subject device may also optionally comprise an interface means for assisting in the introduction of sample into the sample preparation means. For example, where the sample is to be introduced by syringe into the device, the device may comprise a syringe interface which serves as a guide for the syringe needle into the device, as a seal, and the like.

Depending on the particular configuration and the nature of the materials from which the device is fabricated, at least in association with the main electrophoretic flowpath will be a detection region for detecting the presence of a particular species in the medium contained in the electrophoretic flowpath. At least one region of the main electrophoretic flowpath in the detection region will be fabricated from a material that is optically transparent, generally allowing light of wavelengths ranging from 180 to 1500 nm, usually 220 to 800 nm, more usually 250 to 800 nm, to have low transmission losses. Suitable materials include fused silica, plastics, quartz glass, and the like.

The integrated device may have any convenient configuration capable of comprising the enrichment channel and main electrophoretic flowpath, as well as any additional components. Because the devices are microchannel electrophoretic devices, the electrophoretic flowpaths will be present on the surface of a planar substrate, where the substrate will usually, though not necessarily, be covered with a planar cover plate to seal the microchannels present on the surface from the environment. Generally, the devices will be small, having a longest dimension in the surface plane of no more than about 200 mm, usually no more than about 100 mm so that the devices are readily handled and manipulated. As discussed above, the devices may have a variety of configurations, including parallelepiped, e.g., credit card or chip like, disk like, syringe like or any other compact, convenient configuration.

The subject devices may be fabricated from a wide variety of materials, including glass, fused silica, acrylics, thermoplastics, and the like. The various components of the integrated device may be fabricated from the same or different materials, depending on the particular use of the device, the economic concerns, solvent compatibility, optical clarity, color, mechanical strength, and the like. For example, both the planar substrate comprising the microchannel electrophoretic flowpaths and the cover plate may be fabricated from the same material, e.g., polymethylmethacrylate (PMMA), or different materials, e.g., a substrate of PMMA and a cover plate of glass. For applications where it is desired to have a disposable integrated device, due to ease of manufacture and cost of materials, the device will typically be fabricated from a plastic. For ease of detection and fabrication, the entire device may be fabricated from a plastic material that is optically transparent, as that term is defined above. Also of interest in certain applications are plastics having low surface charge under conditions of electrophoresis. Particular plastics finding use include polymethylmethacrylate, polycarbonate, polyethylene terepthalate, polystyrene or styrene copolymers, and the like.

The devices may be fabricated using any convenient means, including conventional molding and casting techniques. For example, with devices prepared from a plastic material, a silica mold master which is a negative for the channel structure in the planar substrate of the device can be prepared by etching or laser micromachining. In addition to having a raised ridge which will form the channel in the substrate, the silica mold may have a raised area which will provide for a cavity into the planar substrate for housing of the enrichment channel. Next, a polymer precursor formulation can be thermally cured or photopolymerized between the silica master and support planar plate, such as a glass plate. Where convenient, the procedures described in U.S. Pat. No. 5,110,514, the disclosure of which is herein incorporated by reference, may be employed. After the planar substrate has been fabricated, the enrichment channel may be placed into the cavity in the planar substrate and electrodes introduced where desired. Finally, a cover plate may be placed over, and sealed to, the surface of the substrate, thereby forming an integrated device. The cover plate may be sealed to the substrate using any convenient means, including ultrasonic welding, adhesives, etc.

Generally, prior to using the subject device, a suitable first or electrophoretic medium will be introduced into the electrophoretic flowpaths or microchannels of the device, where the first medium will be different from the enrichment medium present in the enrichment channel. Electrophoretic media is used herein to refer to any medium to which an electric field is applied to move species through the medium. The electrophoretic media can be conveniently introduced through the reservoirs present at the termini of the electrophoretic flowpaths or directly into the channels or chambers of the electrophoretic flowpaths prior to sealing of the cover plate to the substrate. Any convenient electrophoretic medium may be employed. Electrophoretic media suitable for use, depending on the particular application, include buffers, crosslinked and uncrosslinked polymeric media, organic solvents, detergents, and the like, as disclosed in Barron & Blanch, "DNA Separations by Slab Gel and Capillary Electrophoresis: Theory and Practice," Separation and Purification Methods (1995) 24:1–118, as well as in U.S. patent applications Ser. Nos. 08/636,599 now U.S. Pat. No. 5,883,211 and 08/589,150, now U.S. Pat. No. 5,885,432 and U.S. Pat. No. 5,569,364 the disclosures of which are herein incorporated by reference. Of particular interest as electrophoretic media are cellulose derivatives, polyacrylamides, polyvinyl alcohols, polyethylene oxides, and the like.

The subject invention will now be further described in terms of the figures. FIG. 1 provides a diagrammatic view of an enrichment channel which may find use in the devices of the subject invention. Enrichment channel 10 comprises side walls 1 which enclose reverse phase C18 material 2. Channel 10 further comprise fluid inlets 7 and 4 and fluid outlets 5 and 6. For controlling fluid flow through the channel inlets and outlets, valves 8, 9 and 11 are provided. Glass frits 3 allow for fluid flow through inlet 4 and outlet 5 but restrain reverse phase material 2 in the channel. In using this enrichment channel, sample is introduced through sample inlet 7 in the direction of flowpath 12. As sample moves through channel 10, the analyte comprising fraction is retained on reverse phase material 2 while the remaining waste fraction of the sample flows out waste outlet 6 along flowpath 13. Valves 8 and 9 are closed to prevent sample from flowing or "bleeding" out inlet 4 or outlet 5. After the sample has flowed through channel 10, valve 11 is shut and valves 8 and 9 are opened. Elution buffer is then introduced into channel 10 through glass frit 3 and inlet 4 in the direction of flowpath 14. As elution buffer moves through material 2, the retained fraction of the sample is released and carried with the elution buffer out enriched fraction outlet 5 through frit 3 along flowpath 15.

Figure 2:
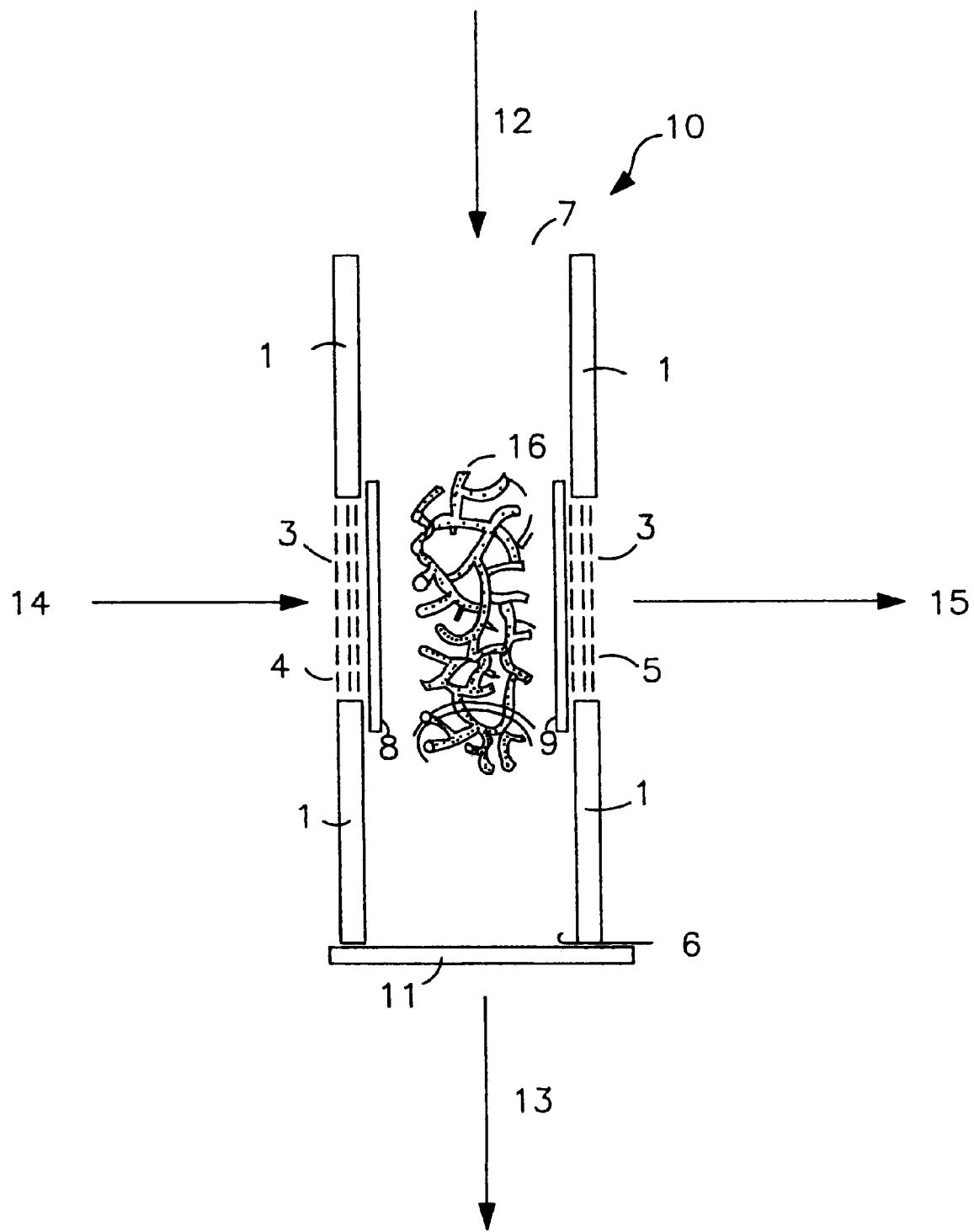
FIG. 2 provides a diagrammatic view of an alternative embodiment of an enrichment channel also suitable for use in the subject device.

In FIG. 2, the same enrichment channel as shown in FIG. 1 is depicted with the exception that reverse phase material 2 is replaced by a network of crosslinked glass filaments 16 to which binding pair member is covalently bound.

Figure 3A:
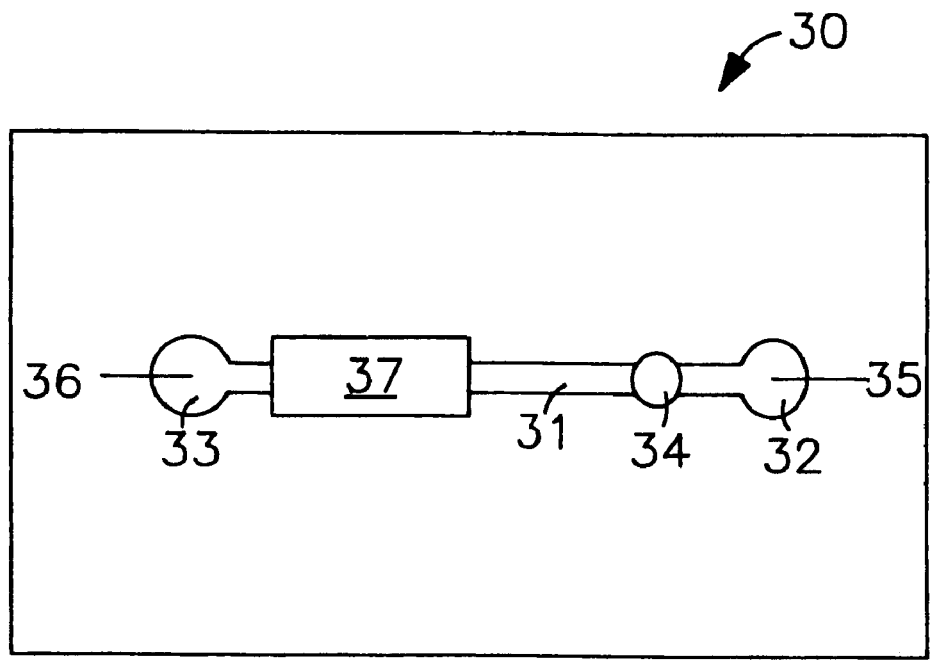
FIG. 3A provides a top diagrammatic view of a device according to the subject invention.

FIG. 3A provides a diagrammatic top view of a credit card shaped (parallelepiped) device according to the subject invention. Device 30 comprises main electrophoretic flowpath 31 having reservoir 32 at a first end and reservoir 33 at a second end. In direct fluid communication with main electrophoretic flowpath 31 is enrichment channel 34 (seen from overhead). Electrodes 35 and 36 are provided for applying an electric field to the medium present in electrophoretic flowpath 31. Detection region 37 is positioned over electrophoretic flowpath 31 for viewing analyte present in the medium comprised in the flowpath. A detection region can also be provided over the enrichment channel 34. Although the device shown in FIG. 3A comprises a single enrichment channel, additional enrichment channels could be provided in the flowpath, including in the detection region.

Figure 3B:
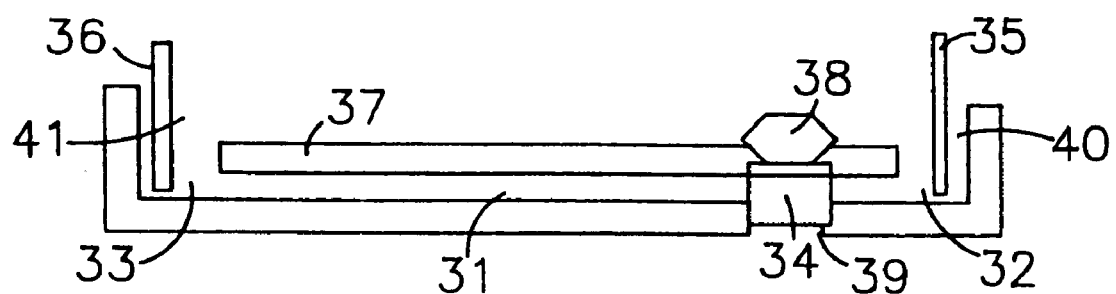
FIG. 3B provides a side view of the device of FIG. 3A.

FIG. 3B provides a diagrammatic side view of the device depicted in FIG. 3A. In using this embodiment of the subject invention, sample is introduced through syringe interface 38 into enrichment channel 34, where the analyte comprising fraction of the sample is retained as the waste fraction flows out of the enrichment channel 34 through discharge outlet 39 and out of the device. Elution buffer is then introduced into reservoir 32 through port 40. An electric field is then applied between electrodes 35 and 36 causing elution buffer to migrate from reservoir 32 through enrichment channel 34 and along electrophoretic flowpath 31 to reservoir 33. As the elution buffer moves through enrichment channel 34, it releases the retained analyte comprising fraction of the initial sample volume and carries it into electrophoretic flowpath 31.

Figure 4:
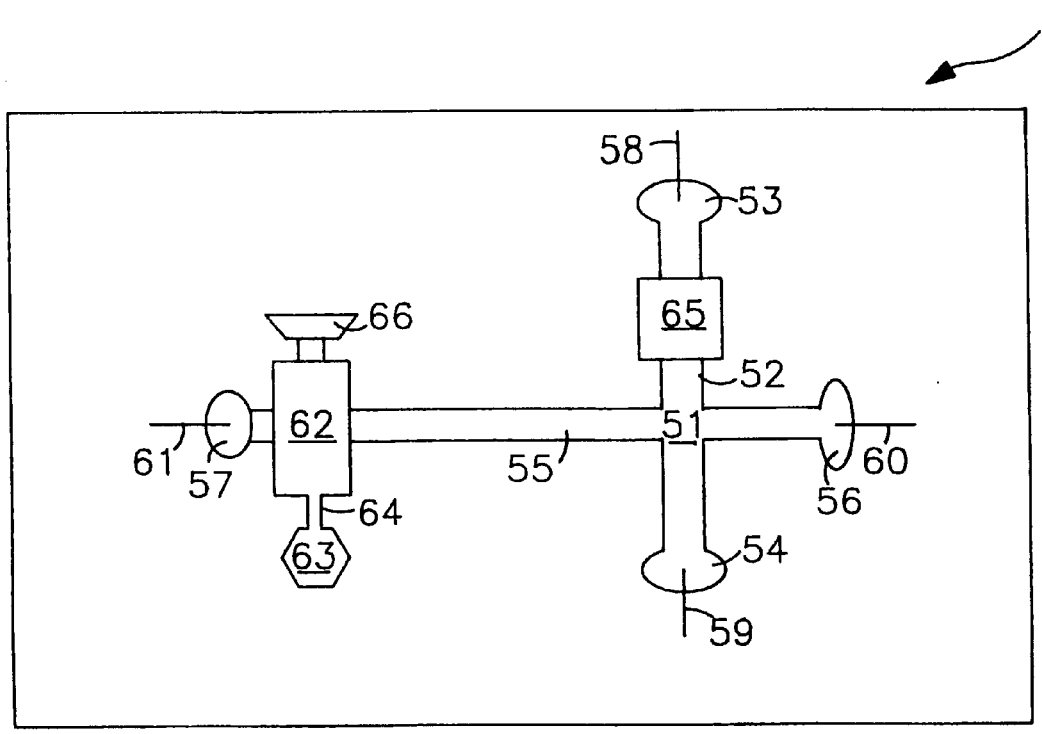
FIG. 4 provides a diagrammatic top view of another embodiment of the subject invention.

FIG. 4 shows a diagrammatic view of an embodiment of the subject invention in which the enrichment channel 62 is separated from main electrophoretic flowpath 52 by secondary electrophoretic flowpath 55. With device 50, sample is introduced into enrichment channel 62 through syringe interface 66. As sample flows through enrichment channel 62, waste sample flows through discharge outlet 64 into waste reservoir 63. An electric field is then applied between electrodes 61 and 60 causing elution buffer present in reservoir 57 to move through enrichment channel 62, resulting in the release of analyte. Analyte is then carried along secondary electrophoretic flowpath 55 along with the elution buffer. When analyte reaches intersection 51, the electric field between electrodes 60 and 61 is replaced by an electric field between electrodes 59 and 58. In this and other analogous embodiments of the subject invention, the time at which analyte reaches intersection 51 may be determined by detecting the presence of analyte in the intersection or by empirically determining the time at which the analyte should reach the intersection, based on the particular nature of the analyte, the medium in the flowpath, the strength of the electric field, and the like. Following application of the electric field between electrodes 59 and 58, which are placed in reservoirs 54 and 53 respectively, the analyte moves from intersection 51 along electrophoretic flowpath 52 towards reservoir 53 and through detection region 65.

Figure 5:
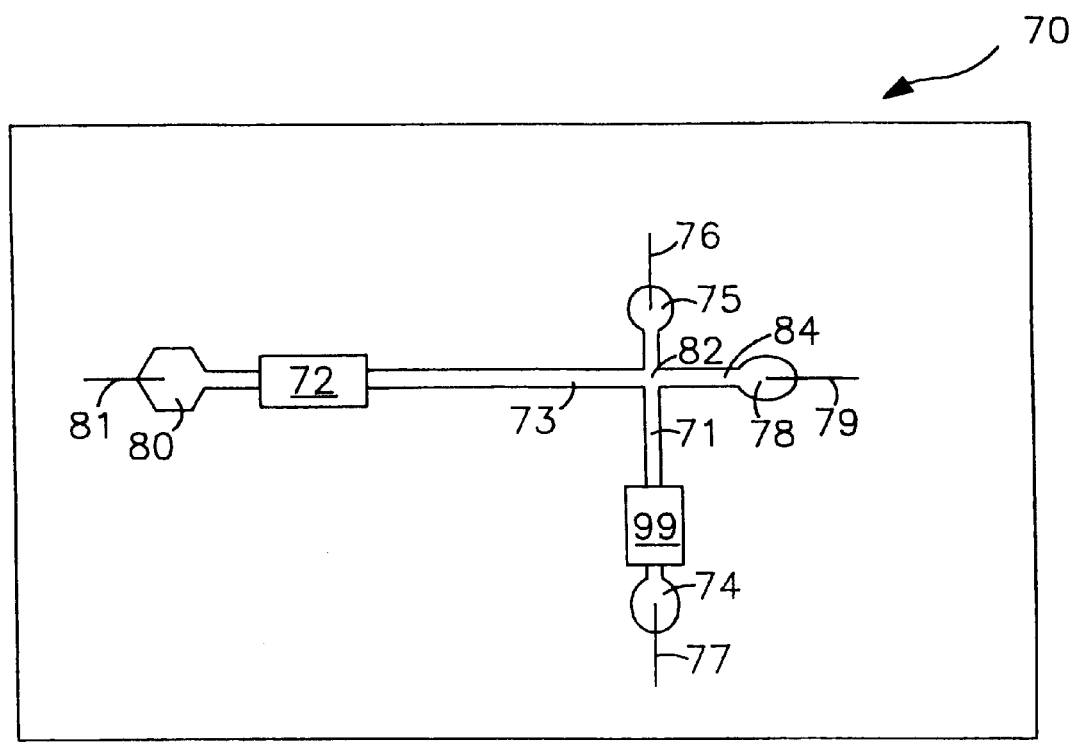
FIG. 5 provides a diagrammatic view of an embodiment of the subject invention in which the enrichment channel comprises a single fluid inlet and outlet.

FIG. 5 provides a diagrammatic top view of yet another embodiment of the subject invention in which the enrichment channel comprises a single fluid inlet and outlet. Device 70 comprises main electrophoretic flowpath 71 in intersecting relationship with secondary electrophoretic flowpath 73. Upstream from the intersection 82 along secondary electrophoretic flowpath 73 is enrichment channel 72. In using this embodiment, sample is introduced through syringe interface 80 into enrichment channel 72, whereby the analyte comprising fraction of the sample is reversibly bound to the material present in the enrichment channel. An electric field is then applied between electrodes 81 and 79 which moves the non-reversibly bound or waste fraction of the sample out of the enrichment channel 72, along secondary electrophoretic flowpath 73, past intersection 82, and out discharge outlet 84 into waste reservoir 78. An elution buffer is then introduced into enrichment channel 72 through syringe interface 80 and an electric field applied between electrodes 81 and 79, causing elution buffer to flow through enrichment channel 72 into secondary flow electrophoretic flowpath 73, carrying analyte along with it. When analyte reaches intersection 82, the electric field between electrodes 79 and 81 is replaced by an electric field between electrodes 76 and 77, which causes analyte to move along main electrophoretic flowpath 71 and towards reservoir 74 through detection region 99.

Figure 6:
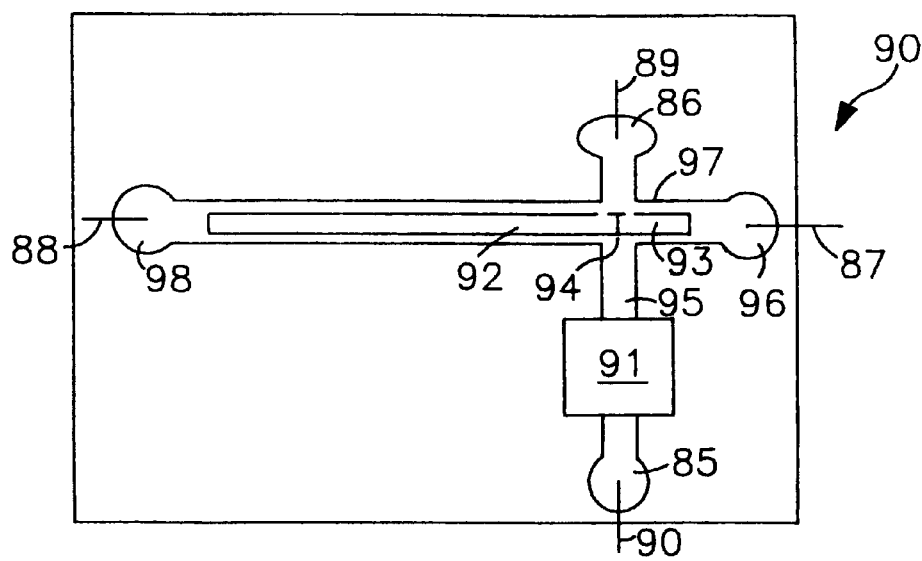
FIG. 6 provides a diagrammatic view of a device according to the subject invention in which the enrichment channel comprises an electrophoretic gel medium instead of the chromatographic material, as shown in FIGS. 1 and 2.

The device shown diagrammatically in FIG. 6 comprises an enrichment channel having an electrophoretic enrichment means, instead of the chromatographic enrichment means of the devices of FIGS. 1 to 5. In device 90, sample is introduced into reservoir 96 and an electric field is applied between electrodes 87 and 88, causing the sample to migrate towards reservoir 98. As the sample migrates towards reservoir 98 it enters stacking gel 93 having a relatively large pore size and travels towards secondary gel 92 of relatively fine pore size. At interface 94, the sample components are compressed into a narrow band. At this point, the electric field between electrodes 87 and 88 is replaced by an electric field between electrodes 89 and 90, which causes the narrow band of sample components at interface 93 to migrate into main electrophoretic flowpath 95, past detection region 91 and towards reservoir 85. In device 90, instead of the stacking gel configuration, one could provide for a molecular size membrane at the region of interface 93, which can provide for selective passage of sample components below a threshold mass and retention at the membrane surface of components in excess of the threshold mass. In yet another modification of the device shown in FIG. 6, present at the location of interface 93 could be an electrode by which an appropriate electric potential could be applied to maintain a sample component of interest in the region of 93, thereby providing for component concentration in the region of 93. For example, for an anionic analyte of interest, upon introduction of sample into reservoir 96 and application of an electric field between 93 and 87, in which 93 is the positive electrode and 87 the ground, the anionic will migrate towards and concentrate in the region of 93. After the analyte has concentrated in the region of electrode 93, an electric field can then be applied between 89 and 90 causing the anionic analyte to migrate towards reservoir 85.

Figure 7:
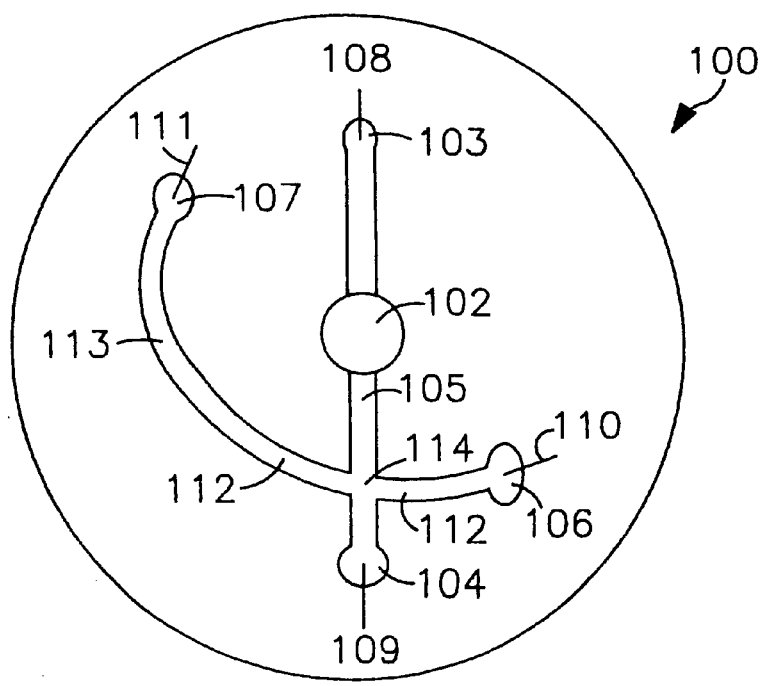
FIG. 7 provides a diagrammatic top view of disk shaped device according to the subject invention.

FIG. 7 provides a top diagrammatic view of a disk shaped embodiment of the subject device, as opposed to the credit card shaped embodiments of FIGS. 3 to 6. In device 100, sample is first introduced into enrichment channel 102. An electric field is then applied between electrodes 108 and 109, moving elution buffer 103 through enrichment channel 102, whereby analyte retained in the enrichment channel 102 is released and carried with the elution buffer to intersection 114. The electric field between 108 and 109 is then replaced with an electric field between 110 and 111, causing analyte to move from intersection 114 along main electrophoretic flowpath 112, past detection region 113 and towards reservoir 107.

Figure 8:
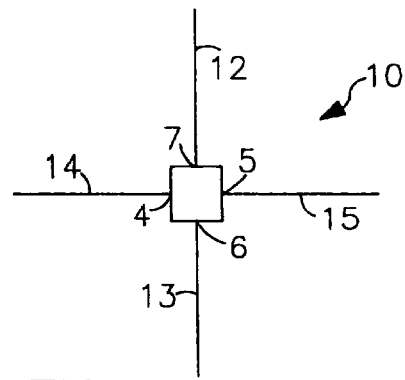
FIG. 8 is a flow diagram of a device as in FIGS. 1 or 2.

Other embodiments may be understood by reference to the flow diagrams in FIGS. 8 through 19, some of which correspond to embodiments shown in the sketches of FIGS. 1 through 7. Referring, for example, to FIG. 8, there is shown a flow diagram of an enrichment channel as shown in FIG. 1 or FIG. 2, with corresponding identification numbers. Accordingly, as described with reference to FIGS. 1 and 2, sample enters enrichment channel 10 through sample inlet 7 by way of flowpath 12. As the sample moves through enrichment channel 10 the fraction containing the fraction of interest is retained on an enrichment medium, which may be, for example, a reverse phase C18 material (as described with reference to FIG. 1) or binding pair members covalently bound to a network of glass filaments (as described with reference to FIG. 2), while the remaining waste fraction flows out through waste outlet 6 along flowpath 13. After a suitable quantity of sample has flowed through enrichment channel 10, flow through inlet 7 and outlet 6 is halted, and elution buffer enters enrichment channel 10 through inlet 4 by way of flowpath 14. Within enrichment channel 10 the retained fraction of interest is released into the elution buffer passing over the enrichment medium, and passes out through enriched fraction outlet 5 by way of flowpath 15.

Figure 9:
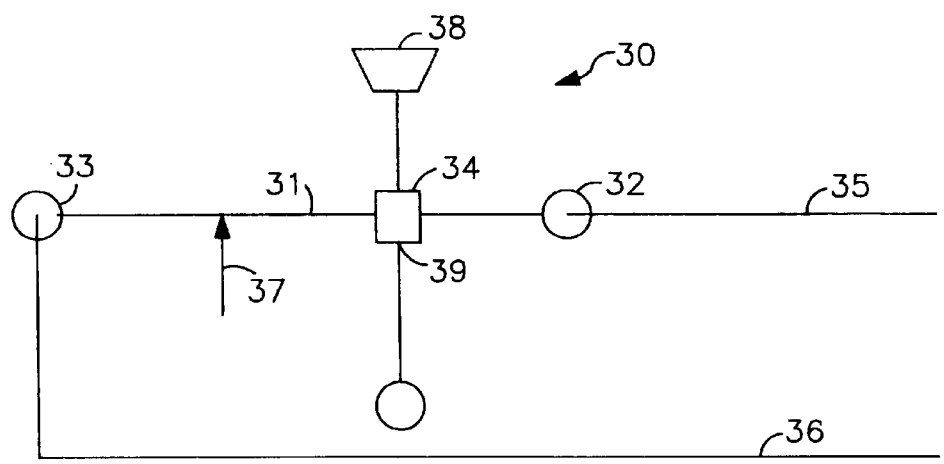
FIG. 9 is a flow diagram of a device as in FIGS. 3A, 3B.

And referring to FIG. 9, there is shown a flow diagram of the embodiment of a device 30 as sketched in two views in FIGS. 3A, 3B and described with reference thereto. In the flow diagrams, the enrichment channel (34 in FIGS. 3A, 3B, 9) is represented by a square; the various reservoirs (e.g., 32, 33 in FIGS. 3A, 3B, 9) are represented by small circles at the ends of the flowpaths (channels), which are represented by lines (e.g., main electrophoretic flowpath 31 in FIGS. 3A, 3B, 9); electrodes (35, 36 in FIGS. 3A, 3B, 9) are represented by hairlines running to the centers of the reservoir circles; an interface for syringe injection (where one may be present; e.g., 38 in FIGS. 3B, 9) is represented by a trapezoid at the end of the sample input flowpath; and the detection region (37 in FIGS. 3A, 3B, 9) is represented by a heavy arrow touching the main electrophoretic channel. Similarly, in FIG. 12, there is shown a flow diagram of the embodiment of a device 90 as sketched in FIG. 6 and described above with reference thereto. In this embodiment, the enrichment channel (120 in FIG. 12) works by electrophoretic enrichment, which results in accumulation of the fraction of interest at the point where the enrichment channel 120 is intersected by the main electrophoretic channel 95. Movement of sample material through the enrichment channel can be accomplished by application of an electrical potential difference between electrodes 87, 88; and elution of the fraction of interest from the enrichment channel through the main electrophoretic channel and to the detection region 91 can be accomplished by application of an electrical potential difference between electrodes 89, 90. As described above with reference to FIG. 6, the accumulation point can be an interface 94 between a stacking gel 93 and a secondary gel 92; and in a further modification, a suitable electrical potential can be applied at an electrode (121 in FIG. 12) at the site of the interface 93 to provide for component concentration in that region of the enrichment channel.

Figure 10:
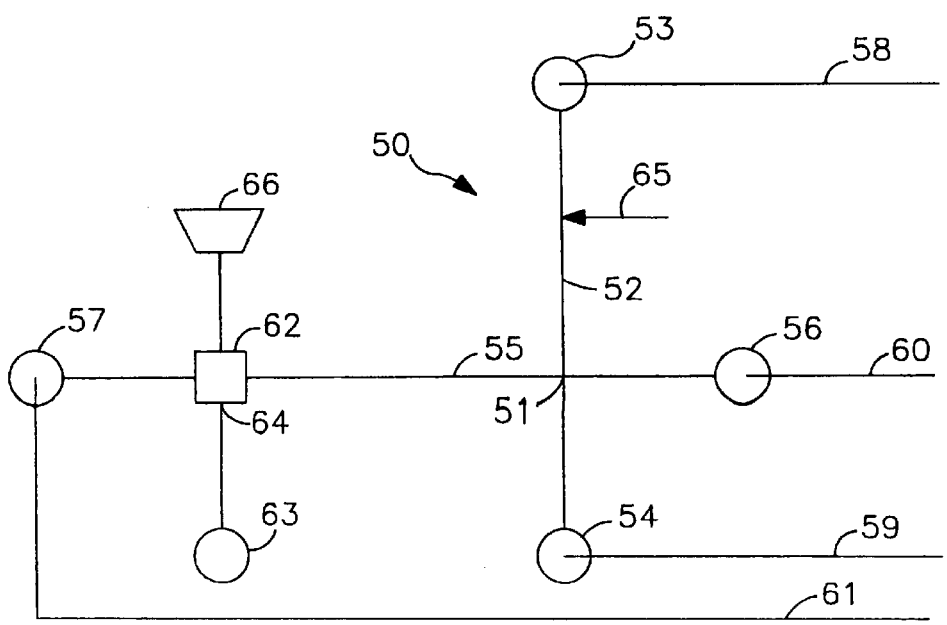
FIG. 10 is a flow diagram of a device as in FIG. 4.
Figure 13:
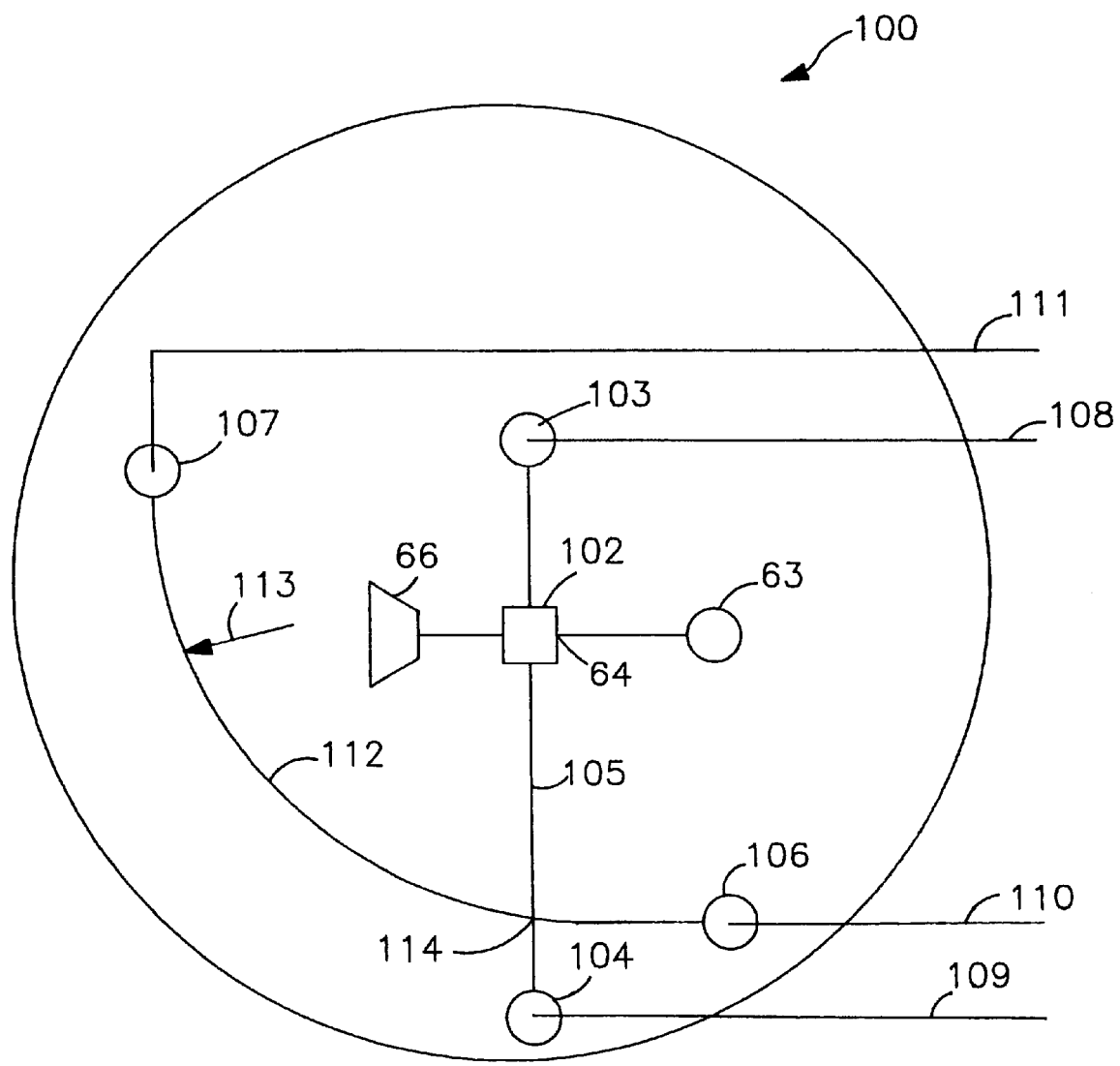
FIG. 13 is a flow diagram of a device as in FIG. 7.
Figure 14:
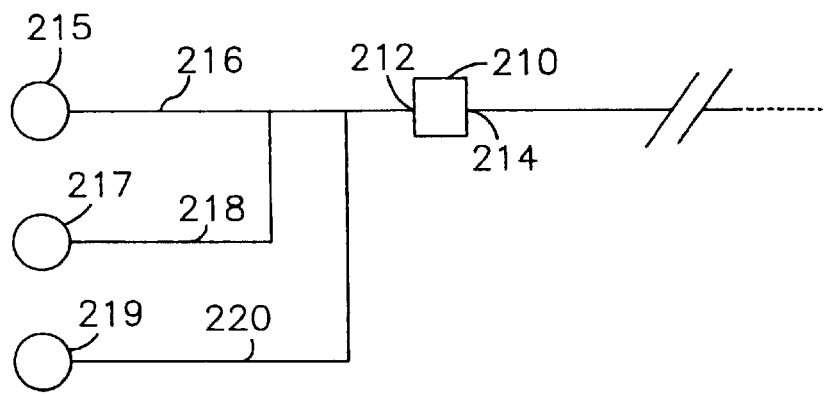
FIG. 14 is a flow diagram of part of an embodiment of a device according to the invention, showing multiple inlets to the separation channel.

FIG. 10 is a flow diagram of the embodiment of a device 50 in which the enrichment channel 62 is separated from main electrophoretic flowpath 52 by secondary electrophoretic flowpath 55, as sketched in FIG. 4 and described above with reference thereto. Similarly, FIG. 13 is a flow diagram of the disc-shaped embodiment of a device 100 as sketched in FIG. 7 and described with reference thereto. FIG. 13 shows the sample input flowpath by which the sample is introduced from the syringe interface 66 into the enrichment channel 102, and the discharge outlet 64 by which waste passes out to waste reservoir 63 while the fraction of interest is retained on the retention medium in the enrichment channel. These features are not shown in the top views of FIG. 7 or FIG. 4.

Figure 11:
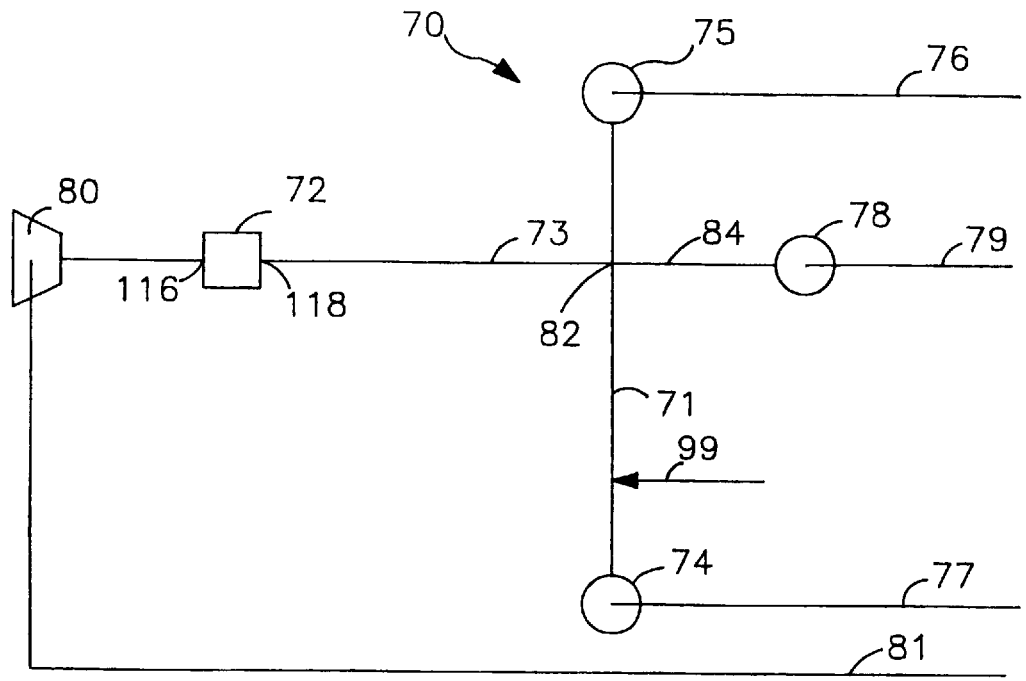
FIG. 11 is a flow diagram of a device as in FIG. 5.

In FIG. 11 there is shown a flow diagram of a device 70, in which there is only one fluid inlet into, and one fluid outlet out from, the enrichment channel 72, as sketched in FIG. 5 and described with reference thereto. During sample injection by way of the syringe interface the fluid inlet 116 serves as a sample inlet and the fluid outlet 118 serves as a waste outlet. While the fraction of interest is retained by the retention medium in the enrichment channel, the waste fraction flows downstream through the secondary electrophoretic flowpath 73, across the intersection 82 of the secondary electrophoretic flowpath with the main electrophoretic flowpath 71, and into discharge outlet 84, which directs the waste away from the mail electrophoretic flowpath 71 toward waste reservoir 78. During elution, elution buffer is injected by way of the syringe interface; fluid inlet 116 serves as an elution buffer inlet and the fluid outlet 118 serves as an enriched fraction outlet to the secondary electrophoretic channel. The fraction of interest moves into the elution buffer in which it is driven electrokinetically in an electric field produced by applying a voltage across electrodes 79, 81 to the intersection of the secondary electrophoretic channel and the main electrophoretic channel. Once the fraction of interest has reached the intersection, a voltage is applied across electrodes 76, 77 to draw the analyte or analytes in the fraction of interest into and along the main electrophoretic flowpath to the detection zone 99.

As noted with reference to FIG. 5, the waste fraction (material not bound to the enrichment medium) can be washed out of the enrichment channel and away from the main electrophoretic pathway by application of an electric field between electrodes upstream from the enrichment channel and downstream from the discharge outlet. That is, prior to introducing the elution buffer to the enrichment channel, a liquid wash medium is passed over the enrichment medium and out through the discharge outlet, carrying away waste fraction components. Any of a variety of materials can be suitable as a wash medium, so long as the wash medium does not substantially elute the fraction of interest from the enrichment medium. Moreover, the wash medium can be chosen to facilitate a selective release or removal, prior to elution, of undesired components that may be bound to or otherwise associated with the enrichment medium. For example, where the components of interest are DNA fragments, the wash medium may contain enzymes that selectively degrade proteins or polypeptides or that selectively degrade RNAs, facilitating the removal of these contaminants away from the fraction of interest prior to elution. Or, for example, where the components of interest are proteins, the wash medium may contain DNAses and RNAses.

Sequential movement of the various liquids into and through the enrichment channel can be readily controlled by providing a reservoir and a flowpath to the upstream part of the enrichment channel for each such liquid. As illustrated in the flow diagram of FIG. 14, for example, an input 212 to enrichment channel 210 is fed by a sample supply flowpath 220 running from a sample reservoir 218, by a wash medium flowpath 218 running from a wash medium reservoir 217, and by an elution medium flowpath 216 running from an elution medium reservoir 215. Movement of these materials can be selectively controlled by application of electrical potentials across electrodes (not shown the Fig.) at the respective reservoirs and at suitable points (as described herein for various configurations) downstream from enrichment channel output 214. Suitable wash media for proteins include, for example, pH-adjusted buffers and organic solvents; and washing can be effected by, for example, adjusting ionic strength or temperature of the wash medium.

Other materials may be introduced to the input flowpath as well, and, particularly, one or more reagent streams can be provided for pretreatment of the sample itself prior to moving it onto the enrichment channel. A crude sample of body fluid (blood, lymphatic fluid, amniotic fluid, cerebrospinal fluid, or urine, for example) can be pretreated by combining the sample with a reagent in the sample flowpath. For example, DNA may be released from cells in a crude sample of whole blood by admixture of a reagent containing an enzyme or a detergent.

Figure 15:
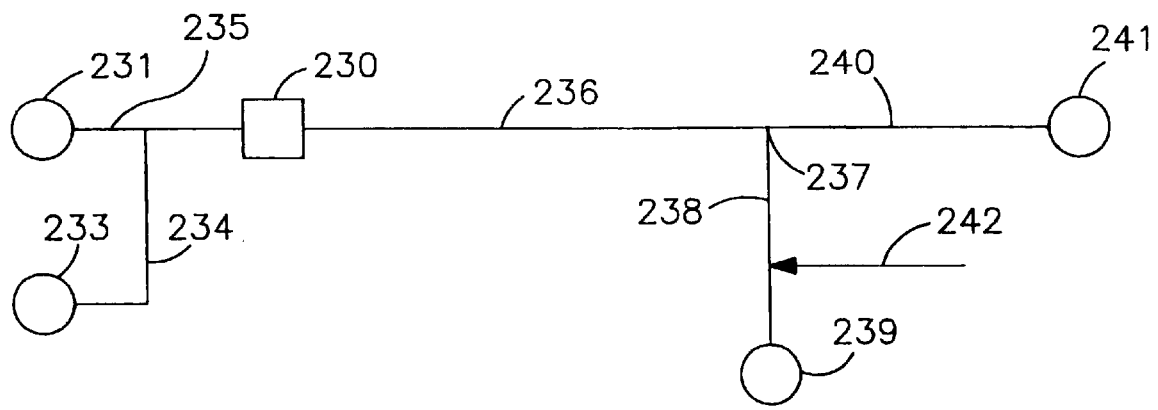
FIG. 15 is a flow diagram of an embodiment of a device according to the invention, showing an alternative configuration for the intersection between the main and secondary electrophoretic flowpaths.

Other flowpath configurations downstream from the enrichment channel can be employed, and certain of these may provide some advantages for particular kinds of downstream treatment or analysis of the components of the fraction of interest. In FIG. 15, for example, the secondary electrophoretic flowpath does not cross the main electrophoretic flowpath; rather, main electrophoretic flowpath 238 joins secondary electrophoretic flowpath 236 at a T intersection (compare, FIG. 12). In this configuration, the upstream arm of the main electrophoretic flowpath runs in the same channel as the secondary electrophoretic flowpath 236. As in other configurations, described herein, sample enters the enrichment channel 230 by way of sample flowpath 234 from sample reservoir 233; and during the enrichment stage the waste fluid passes out from enrichment channel 230 by way of secondary electrophoretic flowpath 236, then past T intersection 237 and away through discharge outlet 240 to waste reservoir 241. Once the enrichment stage is complete, a wash medium may be passed through the enrichment channel and also out through the discharge outlet. The wash medium may be introduced by way of the sample supply flowpath or, optionally, from a separate wash medium flowpath as described above with reference to FIG. 14. Movement of the sample and the wash medium can be accomplished by application of an electric field across electrodes (not shown in the Fig.) at waste reservoir 241 and, respectively, sample reservoir 233 (and, optionally, a wash reservoir). Then, an elution medium can be moved from an elution buffer reservoir 231 by way of elution buffer pathway 235 into and through enrichment channel 230, through secondary electrophoresis pathway 236. Media downstream from the eluting fraction components can be directed away from main electrophoretic flowpath 238 and out by way of waste discharge flowpath 240, until the most downstream component of interest has reached the intersection 237. Then an electrical potential can be applied at reservoir 239 to draw the components from secondary electrophoretic flowpath 236 through intersection 237 and within main electrophoretic flowpath 238 toward and through detection region 242.

Figure 12:
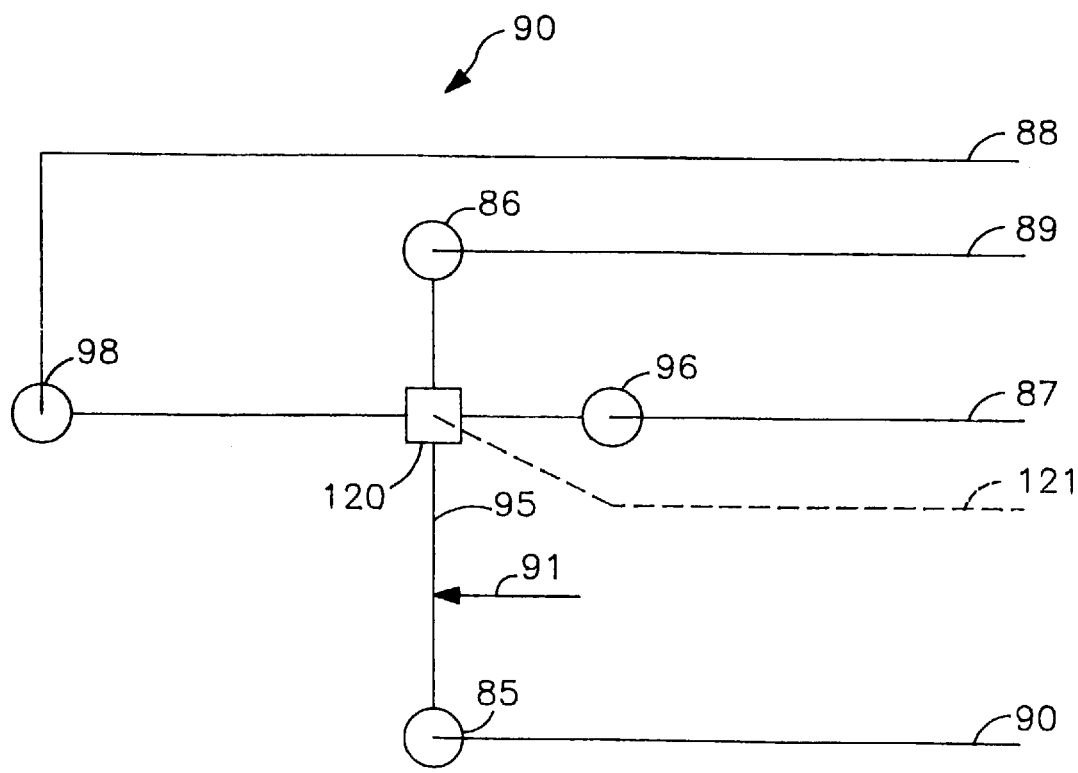
FIG. 12 is a flow diagram of a device as in FIG. 6.

An intersection of the main and secondary electrophoretic flowpaths at an "injection cross", as shown for example in FIGS. 5, 12, can be advantageous where precise metering of the sample plug is desired, as for example, where the main electrophoretic flowpath is used for electrophoretic separation. Such an injection cross can provide for injection from the intersection of a geometrically defined plug of sample components from the fraction of interest.

On the other hand, where precise control of a sample plug is not desirable, and particularly where it is desirable to move the entire eluted sample through the main electrophoretic path way, a T intersection can be preferred. Such a configuration may be advantageous where, for example, the components are analyzed by passing substantially the entire eluted fraction through an array of affinity zones downstream from the intersection.

Figure 16:
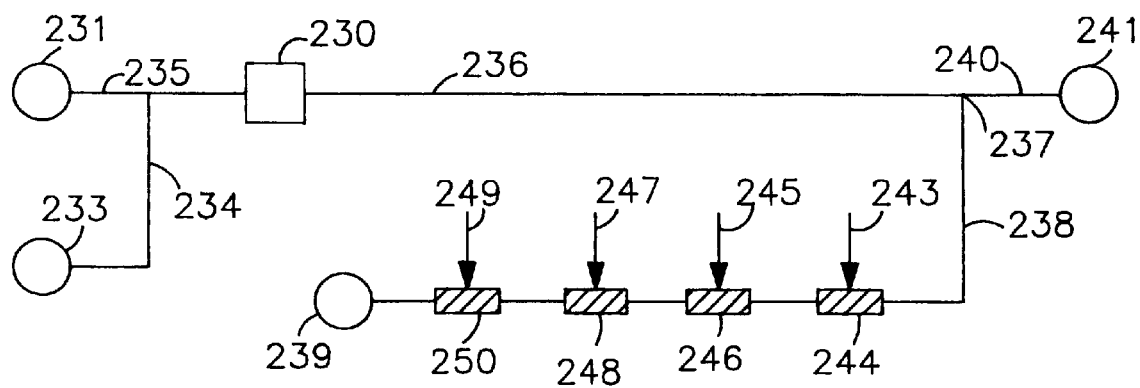
FIG. 16 is a flow diagram of an embodiment of a device according to the invention, showing a plurality of analytical zones arranged in series downstream from the enrichment channel.

By way of example, FIG. 16 is a diagram showing the flow in a configuration having a serial array of affinity zones 244, 246, 248, 250. Each affinity zone is provided with an enrichment medium that has a specific affinity for a selected component of the fraction of interest. For example, the fraction of interest may consist of DNA in a crude cell lysate, wherein the lysate may have been formed upstream from enrichment channel 230 and concentrated and/or purified in enrichment channel 230, so that the eluted fraction that passes into main electrophoretic flowpath 238 consists principally of a complex mixture of DNA fragments of different lengths and base composition. Each hybridization zone is itself an enrichment channel, in which the enrichment medium includes an immobilized oligonucleotide probe having a sequence complementary to a sequence in a target DNA. As the eluted fraction passes serially through the affinity zones 244, 246, 248, 250, any target DNA present in the fraction that is complementary to the probe in one of the affinity zones will become bound in that affinity zone. The affinity zones are provided with detectors 243, 245, 247, 249, configured to detect and, optionally, to quantify, a signal (such as fluorescence or electrochemilluminescence) from components of interest bound in the affinity zones. Any form of biomolecular recognition may be employed as a capture principle in the affinity zones, as the skilled artisan will appreciate. Useful types of affinity include antibody-antigen interactions; binding of poly-dT with adenylated RNA; oligonucleotide probes for RNA, DNA, PNA; streptavidin-biotin binding; protein-DNA interactions, such as DNA-binding protein G or protein A; and molecules having group specific affinities, such as arginine, benzamidine, heparin, and lectins. Other examples will be apparent to the skilled artisan.

Accordingly, for example, the capture principle may include receptor-ligand binding, antibody-antigen binding, etc., and thus the methods and devices according to the invention can be useful for carrying out immunoassays, receptor binding assays, and the like, as well as for nucleic acid hybridization assays.

Figure 17:
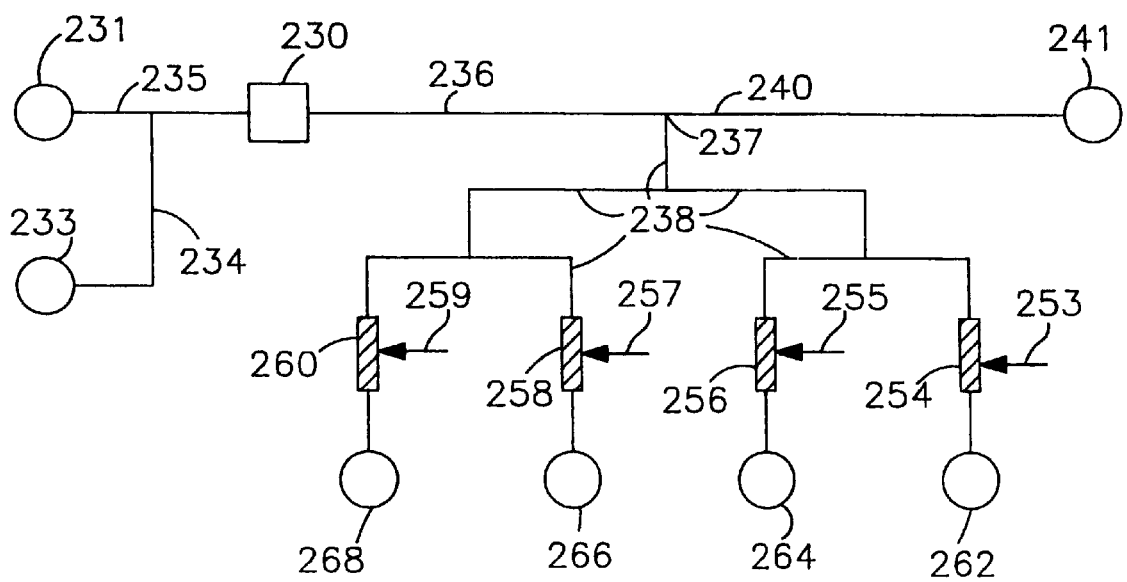
FIG. 17 is a flow diagram of an embodiment of a device according to the invention, showing a plurality of analytical zones arranged in parallel downstream from the enrichment channel.
Figure 18:
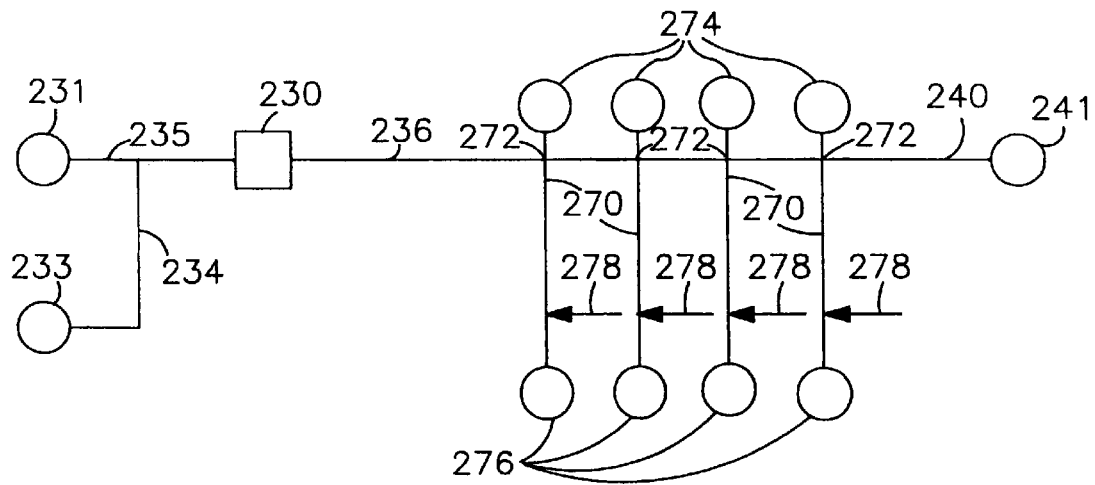
FIG. 18 is a flow diagram of an embodiment of a device according to the invention, showing a plurality of main electrophoretic flowpaths downstream from the enrichment channel.

Alternatively, as mentioned above, the main electrophoretic flowpath can be branched downstream from the intersection with the secondary electrophoretic flowpath, providing a parallel array of main electrophoretic flowpaths, as shown by way of example in FIG. 17. Electrophoretic flowpath 238 is shown as twice bifurcated, so that four main electrophoretic flowpath branches run downstream to their respective waste reservoirs 262, 264, 266, 268. The branches are provided in this example with affinity zones 254, 256, 258, 260, with detectors 253, 255, 257, 259. Pertinent properties of the milieu (such as, e.g., temperature, pH, buffer conditions, and the like) can advantageously be controlled in each flowpath branch independently of the others, as is shown in more detail with reference to FIG. 22, below.

Where the affinity zones are arranged in parallel, as for example in FIG. 17, each affinity zone receives an aliquot of the entire sample that is delivered to the main electrophoresis channel. In this embodiment, sample components that can be captured by two or more of the affinity media will appear in the respective two or more affinity zones. For example, a nucleic acid fragment that contains either one or both of two sequences complementary to two of the probe sequences will, in the parallel arrangement, be captured in the two affinity zones containing those two probes. On the other hand, where the affinity zones are serially arrayed, as for example in FIG. 16, each downstream affinity zone is reached only by sample components not captured by an affinity zone upstream from it. Here, for example, a nucleic acid fragment that contains both of two sequences complementary to probe sequences in two of the affinity zones will be captured only in the more upstream of the two affinity zones. This arrangement may be advantageous where it is desirable to identify sample components that contain one but not another moiety or sequence.

And alternatively, as noted above, a plurality of main electrophoretic flowpaths may be provided for treatment of the enriched eluted sample. As shown by way of example in FIG. 18, the main electrophoretic flowpaths 270 may carry eluted sample fraction from the secondary electrophoretic flowpath 236 through a series of intersections 272. Each main electrophoretic flowpath 270 is provided with reservoirs upstream (274) and downstream (276) and each is provided with a detector 278. This configuration may be employed to run a set of tests or assays or measurements on aliquots of a single enriched sample fraction, and will be particularly useful where, as noted above, precise metering of the quantity of analyte is desirable. As will be appreciated, each of the main electrophoretic flowpaths 270 can be provided with an affinity zone or with an array of affinity zones (not shown in FIG. 18) as described above with reference to FIGS. 16, 17.

Figure 19:
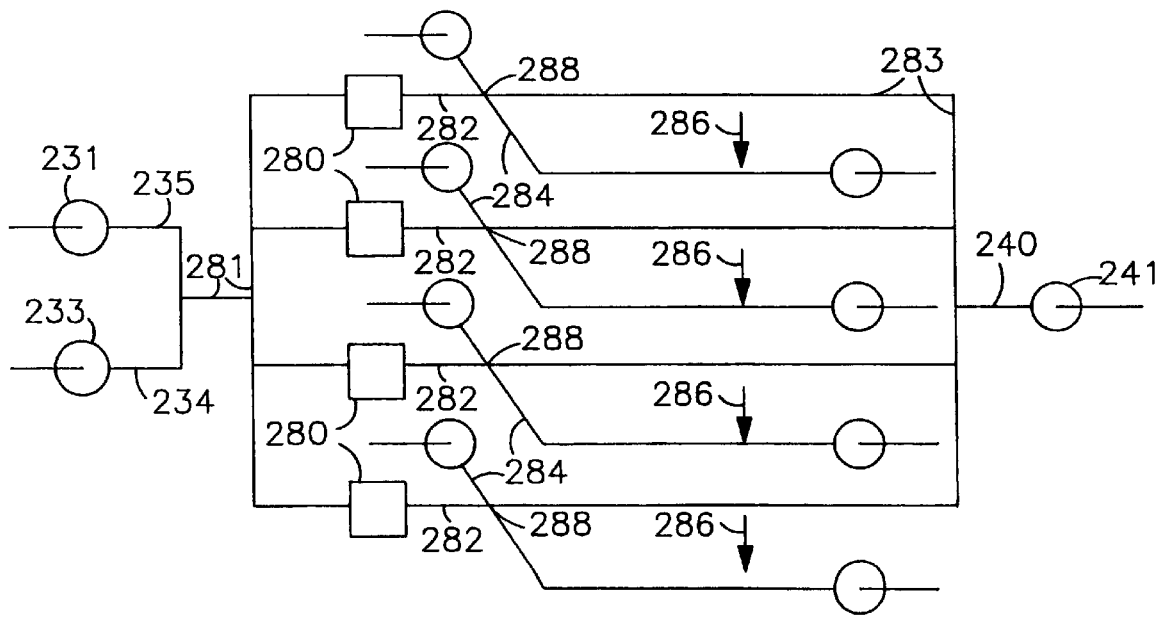
FIG. 19 is a flow diagram of an embodiment of a device according to the invention, showing a plurality of enrichment channels arranged in parallel.

Or, as shown by way of example in FIG. 19, a plurality of enrichment channels 280 can receive sample from a branched sample supply manifold 281. Each enrichment channel 280 can during the elution stage deliver an enriched fraction to an intersection 288 with a main electrophoretic flowpath 284. During the enrichment stage (and optionally during a wash stage) waste fraction is carried away from the intersections 288 by way of a branched discharge manifold 283 and out through discharge outlet 240 to waste 241. Such an arrangement can be used to particular advantage, for example, where the fraction of interest is a mixture of DNAs, and where it is desirable to obtain both sequence information and size information for the DNAs. The configuration of FIG. 19 can be used, for example, for a flow-through analysis analogous to a Southern blot analysis. In the conventional Southern blot analysis, DNA fragments are first separated on a gel, and then transferred to a membrane on which probes are allowed to bind complementary fragments. The Southern blot analysis is practiced mainly as a manual bench-top procedure, and is highly labor-intensive, taking several days to complete. The flow-through analysis, according to the invention, can be substantially automated, and the analysis can be completed much more rapidly.

In the flow-through analysis, each but one of the enrichment channels is provided with a sequence-specific capture medium, such as a sequence-specific immobilized oligonucleotide probe, and the last one of the enrichment channels is provided with a generic capture medium which binds all DNA fragments in the sample. These different enriched fractions are delivered to the intersections 288 during the elution stage, and then they are moved electrophoretically in the respective main electrophoretic flowpaths 284, each provided with a detector 286. The enriched fraction from the enrichment channel containing a generic capture medium contains a mixture of all sizes of DNAs from the sample, having a range of electrophoretic mobilities, passing the detector sequentially, and resulting in a series of signal peaks. The enriched fraction from each of the other enrichment channels contains only DNAs complementary to the specific capture medium in its respective enrichment channel.

Figure 20:
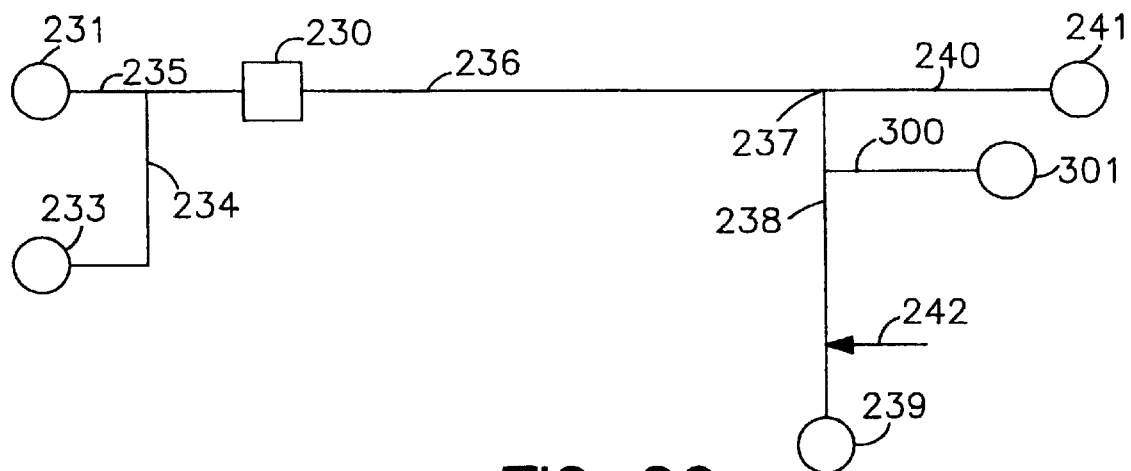
FIGS. 20 and 21 are flow diagrams of embodiments of a device according to the invention, similar to those shown in FIGS. 15 and 16, respectively, and additionally having a reagent flowpath for carrying a reagent from a reservoir directly to the main electrophoretic flowpath.

In some embodiments it may be desirable to combine one or more reagents with the enriched fraction downstream from the intersection of the secondary flowpath and the main electrophoretic flowpath. FIG. 20 is a flow diagram similar to one shown in FIG. 15. In FIG. 20 a reagent flowpath 300 carries a reagent (or reagents) from a reservoir 301 to the main electrophoretic flowpath 238, where the reagent can combine with and react with one or more analytes in the enriched fraction. And, as will be appreciated, where the main electrophoretic flowpath is branched downstream from the intersection with the secondary electrophoretic flowpath, producing subfractions in the branches, each such downstream branch can be provided with a reagent flowpath carrying reagent from a reservoir. Such a configuration can provide either for replicate treatment of the subfractions with a single reagent, or for treatment of each subfraction with a different reagent, or for simultaneous treatment of subfractions with two or more reagents, each producing a particular desired result upon interaction with the analyte(s) in the enriched subfraction.

Figure 21:
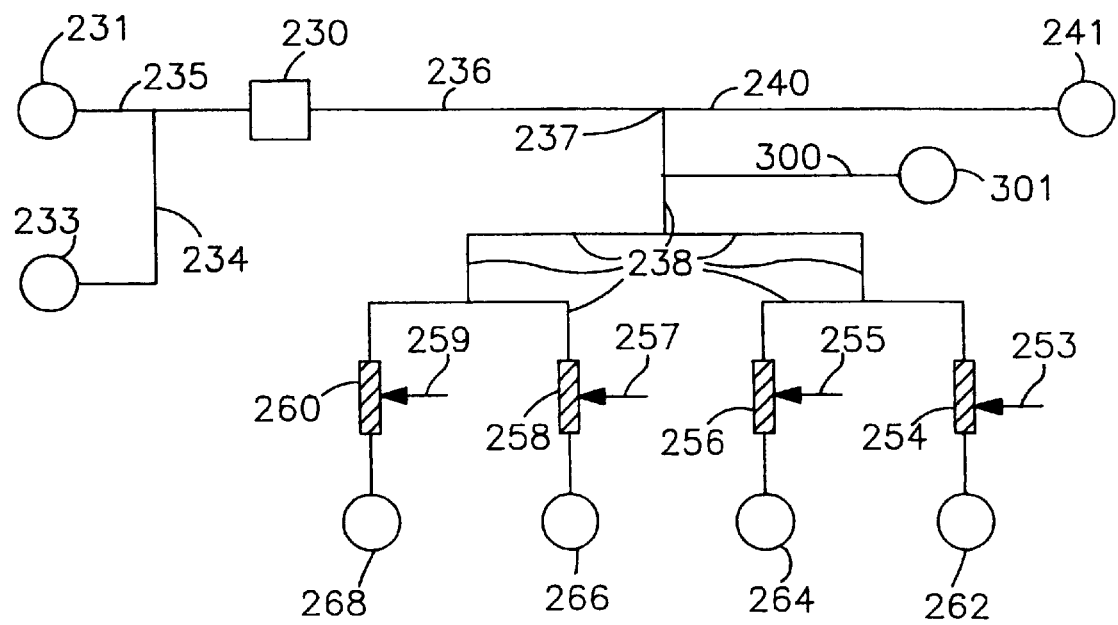
Figure 22:
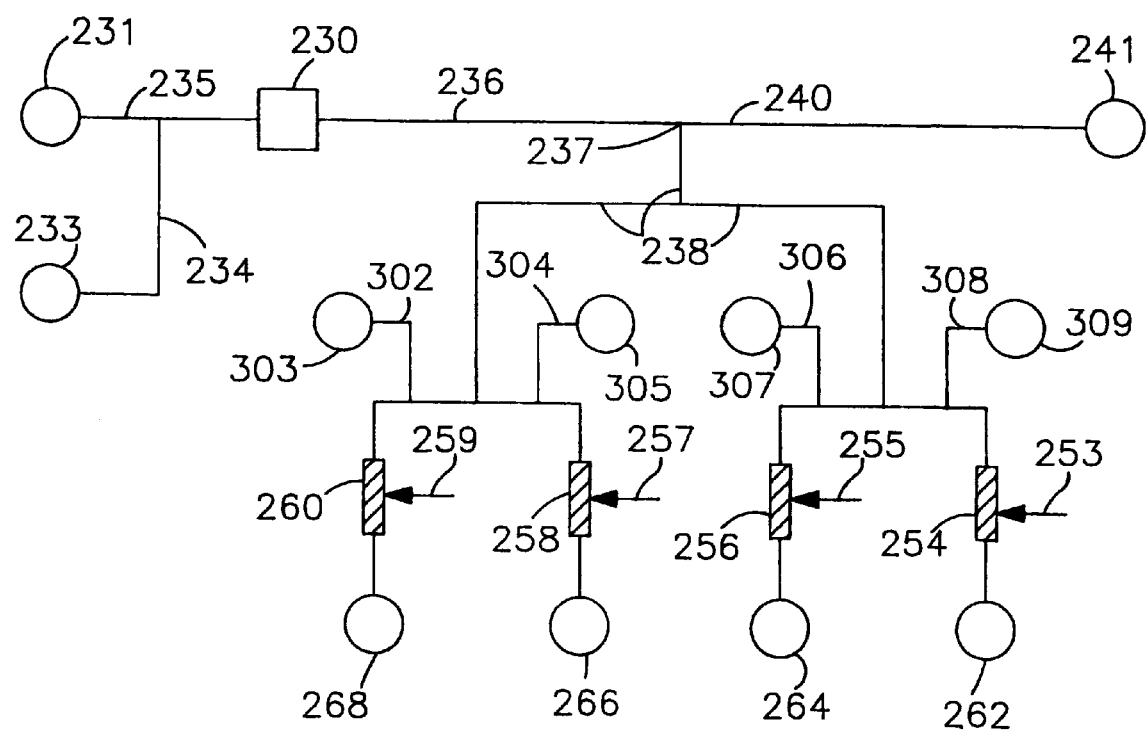
FIG. 22 is a flow diagram of an embodiment of a device according to the invention, similar to that shown in FIG. 17, respectively, and additionally having a plurality of reagent flowpaths for carrying a reagent from a reservoir directly to downstream branches of the main electrophoretic flowpath.

FIGS. 21 and 22 are flow diagrams similar to those shown in FIGS. 16 and 17, having multiple branched main electrophoretic flowpaths, each branch provided with an affinity zone. In FIG. 21 reagent flowpath 300 carries a reagent (or reagents) from a reservoir 301 to the main electrophoretic flowpath 238, where the reagent can combine with and react with one or more analytes in the enriched fraction. In this embodiment, because the reagent flowpath 300 intersects the main electrophoretic flowpath 238 at a point upstream from the first bifurcation, the reagent supplied by reservoir 301 effects a replicate treatment of all the subfractions that are treated on the downstream branches and detected in the respective affinity zones. In FIG. 22, each of the downstream branches of the main electrophoretic flowpath 238 is provided with reagent flowpath (302, 304, 306, 308) each carrying a reagent from a separate reagent reservoir (303, 305, 307, 309). Such a configuration can provide for different treatment of the subfractions, for example, providing independent stringency control of parallel hybridization zones.

For example, devices providing flowpaths as in any of FIGS. 18 through 22, or a combination of these, can be used for DNA profiling. More specifically, for example, restriction fragment polymorphism ("RFLP") analysis can be carried out by employing a plurality of different single-locus RFLP probes in reservoirs 303, 305, 307 and 309 as shown in FIG. 22. By running a large number of probes in parallel, the resulting distribution of alleles should yield a rapid and representative DNA profile, while significantly minimizing the possibility of random matches.

The subject devices may be used in a variety of applications, where one or more electric fields are applied to a medium to move entities through the medium. Representative applications include electrophoretic separation applications, nucleic acid hybridization, ligand binding, preparation applications, sequencing applications, synthesis applications, analyte identification applications, including clinical, environmental, quality control applications, and the like. Thus, depending on the particular application a variety of different fluid samples may be introduced into the subject device, where representative samples include bodily fluids, environmental fluid samples, e.g., water and the like, or other fluid samples in which the identification and/or isolation of a particular analyte is desired. Depending on the particular application, a variety of different analytes may be of interest, including drugs, toxins, naturally occurring compounds such as peptides and nucleic acids, proteins, glycoproteins, organic and inorganic ions, steroids, and the like. Of particular interest is the use of the subject devices in clinical applications, where the samples that may be analyzed include blood, urine, plasma, cerebrospinal fluid, tears, nasal or ear discharge, tissue lysate, saliva, ocular scratches, fine needle biopsies, and the like, where the sample may or may not need to be retreated, i.e., combined with a solvent to decrease viscosity, decrease ionic strength, or increase solubility or buffer to a specific pH, and the like, prior to introduction into the device. For clinical applications, analytes of interest include anions, cations, small organic molecules including metabolites of drugs or xenobiotics, peptides, proteins, glycoproteins, oligosaccharides, oligonucleotides, DNA, RNA, lipids, steroids, cholesterols, and the like.

The following examples are offered by way of illustration and not by way of limitation.

EXAMPLES

Example 1

High Efficiency Separation of Organic Analytes in an Aqueous Sample.

A card as shown in FIG. 4 is used in the separation of organic analytes in an aqueous sample as follows in conjunction with a device that provides for the application of appropriate electric fields through introduction of electrodes into each reservoir of the card and provides for a means of detecting analyte as it passes through detection region 65. In Card 50, the enrichment channel 62 comprises porous beads coated with a C-18 phase, while the reservoirs and channels, except for the waste reservoir, comprise 20 millimolar borate buffer. A 100 $\mu$l aqueous sample is injected into enrichment channel 62 through interface 66. Substantially all of the organic analyte in the sample reversibly binds to the C18 coated porous beads, while the remaining sample components flow out of enrichment channel 62 into waste reservoir 63. 10 $\mu$l of an elution buffer (90% methanol/10% 20 millimolar borate buffer pH 8.3) are then introduced into the enrichment channel 62 through interface 66, whereby the reversibly bound organic analyte becomes free in the elution buffer. Because of the small volume of elution buffer employed, the concentration of analyte in the volume of elution buffer as compared to the analyte concentration in the original sample is increased 100 to 1000 times. The seals over reservoirs 57 and 56 are then removed and an electric field is applied between electrodes 61 and 60, causing buffer present in 57 to move towards 56, where movement of the buffer front moves the elution plug comprising the concentrated analyte to intersection 51. A voltage gradient is then applied between electrodes 58 and 59, causing the narrow band of analyte present in the volume of elution buffer to move through separation channel 52, yielding high efficiency separation of the organic analytes.

The above experiment is also performed in a modified version of the device depicted in FIG. 4. In the modified device, in addition to reservoir 57, the device comprises an elution buffer reservoir also in fluid communication with the enrichment channel 62. In this experiment, sample is introduced into enrichment channel 62, whereby the organic analytes present in the elution buffer reversibly bind to the C18 phase coated beads present in the enrichment channel. An electric field is applied between an electrode present in the elution buffer reservoir and electrode 60 for a limited period of time sufficient to cause 10 µl of elution buffer to migrate through the enrichment channel and release any reversibly bound organic analyte. After the elution buffer has moved into the enrichment channel, a voltage gradient is then applied between electrodes 61 and 60, resulting in the movement of buffer from 57 to 56, which carries the defined volume of organic analyte comprising elution buffer to intersection 51, as described above.

Example 2
Sample Enrichment Employing Paramagnetic Beads for Enrichment within an Integrated Microfluidic Device.

Figure 23:
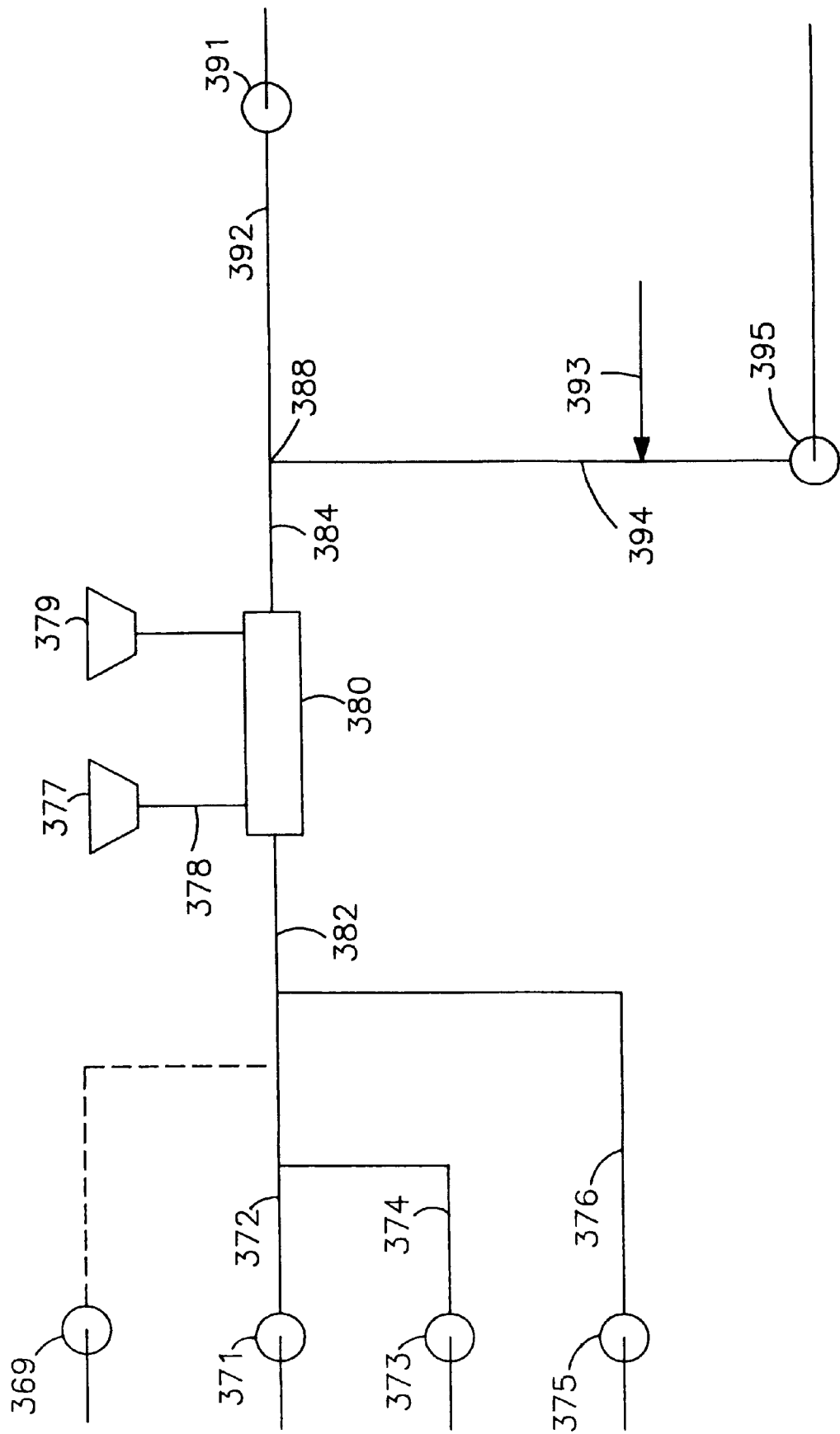
FIG. 23 is a flow diagram of an embodiment of a device according to the invention, in which the enrichment medium includes coated magnetic beads.

Experimental protocols based on biomagnetic separation methods are provided as embodiments of the current invention. In a microfluidic device configured generally as illustrated in FIG. 23, and described with reference thereto, a crude sample composed of a particular target is treated using magnetic beads, coated with an affinity medium, to capture a target having a binding affinity for the specific affinity medium. Such magnetic beads are marketed, for example, by Dynal, Inc. New York, under the name Dynabeads®. Dynabeads are superparamagnetic, monodispersed polystyrene microspheres coated with antibodies or other binding moieties that selectively bind to a target, which may be or include cells, genes, bacteria, or other biomolecules. The target-Dynabead complex is then isolated using a magnet. The resulting biomagnetic separation procedure is simple, rapid and reliable, whereby the Dynabeads serve as a generic enrichment medium for isolating specific targets from complex heterogeneous biological mixtures. Such magnetic enrichment media may be employed according to the invention in a wide variety of applications involving cell biology, molecular biology, HLA tissue typing, and microbiology, for example. Two illustrative examples are provided here, specifically, methods for DNA purification and cell isolation.

First, the microchannel-based device is generally described, and then the method of employing Dynal beads for biomagnetic separation is generally described.

The integrated microfluidic device, as shown by way of example in FIG. 23, includes a main electrophoretic flowpath 394 coupled to an enrichment channel 382, which includes a solid phase extraction (SPE) chamber 380, and which is connected to downstream waste reservoir 391. The main electrophoretic flowpath, which consists of an enriched-sample detection region 393 and fluid outlet reservoir 395, joins the secondary electrophoretic flowpath 384 at a T intersection 388. In this configuration, sample handling is achieved electrokinetically by controlling the electric potential across the appropriate electrodes placed within the inlet reservoirs for the wash 373 and elution 375 buffers and outlet reservoirs 391 and 395.

The Dynabeads and then the sample of interest are introduced into the device through injection inlet ports 379 and 377, respectively. Within the enrichment chamber, the heterogeneous suspension of sample and Dynabeads specific for a given target incubate allowing the Dynabeads to bind the target by specific absorption to the particular capture moieties on the surface of the beads. Immobilization of the target-bead complex to the side of enrichment chamber 380 is achieved magnetically. This is possible manually by placing a rare earth permanent magnet adjacent to the enrichment chamber. In another embodiment of the invention, an automated protocol employing electromagnetic means is used to control the applied magnetic field imposed on the SPE chamber.

Upon completion of the magnetic immobilization step, a wash medium contained within wash buffer reservoir 373 can be moved via pathway 374 into and through enrichment channel 380. During sample rinsing, the waste fluid passes out from the enrichment chamber 380 by way of the electrophoretic flow path 384, then past the T intersection 388 and away through the discharge outlet 392 to waste reservoir 391. Thus, the supernatant from the wash steps is removed from the system without having to pass the waste through the main electrophoretic channel 394. This embodiment of the invention affords an advantageous means for isolating and enriching the target biomolecule from a crude sample without first contaminating the detection region 393.

Example 3
DNA Purification from Whole Blood.

An experimental method employing an electrophoretic microdevice as schematically represented in FIG. 23 is provided in which Dynal® biomagnetic beads are used as an enrichment medium for extracting and purifying genomic DNA from whole blood. The source of blood may be a small dried forensic sample on a slide (e.g., on the order of a nanogram), an aliquot of freshly drawn arterial blood (as small as 10 µl) or bone marrow (approximately 5 µl). A protocol amenable to rapid DNA isolation and elution will be provided for the purpose of demonstrating an automated procedure for treating whole blood on-board the device of FIG. 23 so as to yield aliquots of DNA for amplification and analysis or for direct analysis without amplification. The process includes the following steps:

1. reagent and sample loading;
2. cell lysis/DNA capture;
3. repetitive DNA washes; and
4. DNA elution.

Each of these steps will now be discussed in more detail.

For this embodiment in which commercially packaged reagents are being used, loading of the biomagnetic separation media, lysis solution and sample is achieved by means of specially designed injection ports to accommodate differences in the reagents and sample. The Dynal DIRECT™ reagents, which include the lysis solution and magnetic beads, are first injected directly into the solid phase extraction chamber 380 via manual injection port 379, followed by manual injection of the blood sample into the SPE chamber via the injection port 377. Alternatively, other commercial reagents may be used where the nuclei lysis solution and beads are not packaged together as a kit but are instead supplied separately. In this case, a lysis solution can be electrokinetically loaded into the SPE chamber 380 from the inlet reservoir 371. Magnetic beads, supplied for example by Japan Synthetic Rubber, are next loaded either from the injection port 379 or electrokinetically from inlet reservoir 369. For the latter approach, the beads are confined to the chamber by electromagnetic capture, mechanical means (e.g., membrane, mesh screen, or agarose gel plug) placed just downstream of the SPE chamber in flowpath 384, or both. Once the chamber is filled with beads and lysis solution, the DNA sample is added via the injection port 377, or electrokinetically via a sample inlet reservoir provided with an electrode pair with an electrode downstream from the chamber.

Within the enrichment chamber, the blood sample, lysis solution and Dynabeads are allowed to incubate for five minutes during which the cells are lysed. Released nucleic acids can then absorb to the capture moieties immobilized on the surface of the microparticles to form a DNA-bead complex. To enhance cell lysis, mixing can be achieved by, for example, arranging the supply channels so that the streams of beads, sample, and lysis solution merge. Mixing can be enhanced electrokinetically by judicious control of the applied electric field. By periodically reversing the polarity of the electrodes placed in the inlet and outlet reservoirs 371 and 391, respectively, it is possible to electrokinetically move the blood-lysis buffer mixture in an oscillatory manner within the SPE chamber. To increase further the mechanical shear applied to the cells, aperture-like structures can be molded into the SPE chamber housing.

Following the magnetic isolation and capture of the DNA-bead complex at the side of the SPE chamber, rinsing is achieved by electrokinetic transport of the wash buffer solution contained in reservoir 373 through the chamber and out to the waste reservoir 391. After this 45 second rinse, the beads are resuspended into solution by releasing the magnetic field and then allowed to incubate for one minute in the wash buffer. Following the same protocol, rinsing is repeated two more times, allowing the cell lysate and supernatant from each of the wash steps to be removed from the system without having to pass the waste, including PCR inhibitors, through the main electrophoretic channel 394.

The final step of the purification process is DNA elution. Again, the capture beads with bound DNA are immobilized electromagnetically before the elution buffer is electrokinetically transported from reservoir 373 into the SPE chamber. To obtain quantitative elution, precise manipulation of electrode potentials is necessary, not to allow the buffer to pass through the chamber and thus prematurely wash away the purified DNA. Alternatively, a plug of elution buffer may be moved into the chamber by employing an injection cross (not shown in FIG. 23) as described in D. Benvegnu et al. U.S. patent application Ser. No. 08/878,447, filed Jun. 18, 1997, now U.S. Pat. No. 5,900,130. With the elution buffer in the SPE chamber, the beads are resuspended by releasing the magnetic field and then allowed to incubate in the elution buffer for two minutes allowing for finite DNA desorption kinetics. Upon completion of DNA elution, the beads are immobilized electromagnetically in the SP chamber and the purified DNA is electrokinetically injected as a plug into the main electrophoretic channel 394 for analysis. The detection region 395 can represent an elaborate microfluidic system (not shown in FIG. 23) which may be comprised of a plurality of microchannels for restriction enzyme digestion, blot hybridizations, including Southern and slot/dot blots, electrophoretic fragment sizing, and quantitative PCR analysis, among others. These embodiments of the invention will not, however, be discussed further in this example.

In summary, the above protocol allows for isolation of PCR-ready aliquots of purified DNA in less than ten minutes and without user intervention once the crude sample is introduced to the microfluidic device. Other advantages of the method include the minute amount of reagents that are consumed in a given experiment, in addition to not requiring more labor intensive precipitation or centrifugation steps. ADD others.

Example 4
Cell Enrichment Employing Immunomagnetic Isolation.

An experimental protocol where Dynal® biomagnetic beads are used as an enrichment medium for isolating cell targets is provided. The procedure is similar to that described above for DNA purification. As in example 3, the target is selectively captured by beads coated with specific binding moieties immobilized on the surface of the paramagnetic microparticles. Dynabeads are available prepared in various forms, as follows:

1. precoated with affinity purified monoclonal antibodies to many human cell markers, including T cells, T cell subsets, B cells, monocytes, stem cells, myeloid cells, leukocytes and HLA Class II positive cells;
2. coated with secondary antibodies to mouse, rat, or rabbit immunoglobulins for the isolation of rodent B cells, T cells and T cell subsets;
3. in uncoated or tosylactivated form for custom coating with any given biomolecule; or
4. in streptavidin-coated form for use with biotinylated antibodies.

In a microfluidic device configured generally as illustrated in FIG. 23, a heterogeneous suspension of cells is treated employing electrokinetic and magnetic manipulation methods to prepare purified aliquots of cells for further processing and analysis. Biomagnetic separation is possible manually or in an automated format employing electromagnetic control of the magnetic field imposed on the SPE chamber. The following four step protocol is provided as a representative embodiment of the invention.

1. loading of target cells and reagents, including biomagnetic separation media: load the solution of magnetic beads into SPE chamber 380, either directly via injection port 379, or electrokinetically from the inlet reservoir 371 containing solution of Dynal beads specific to a given target; or add sample directly to SPE chamber filled with solution of Dynabeads by means of sample injection port 377.

2. cell capture employing Dynabeads capable of binding specific target:
   allow sample and beads to incubate for 2.5 minutes within the SPE chamber, enhance adsorption by employing an electrokinetic mixing step, target cells bind to Dynabeads to form target-bead complex.

3. target cell wash by immobilizing the bead-target cell complex:
   electromagnetically immobilize capture beads that contain the bound target, rinse with wash buffer solution by electrokinetic manipulation:
   remove supernatant by controlling electrode potentials so as to pass wash buffer from inlet reservoir 373 through the SP chamber to waste outlet 391,
   stop the flow after 45 seconds and resuspend target-bead complex into solution by releasing magnetic field,
   incubate the target-bead complex in wash buffer for one minute,
   repeat above wash steps two more times.

4. target cell elution employing Dynal's DETACHaBEAD™ reagents:
   immobilize capture beads electromagnetically, load the DETACHaBEAD™ solution into SP chamber 380:
   electrokinetically move the Dynal antibody-based reagent from the elution buffer reservoir 373 by manipulation of electrode potentials to avoid allowing the elution buffer to pass through the chamber, or, alternatively, an injection cross (not shown in FIG. 22) can be used to inject a plug of elution buffer into the SP chamber,
   resuspend beads by releasing magnetic field,
   incubate suspended beads in elution buffer for two minutes to allow for finite desorption kinetics,
   upon completion of target elution, immobilize beads electromagnetically isolated target cells can be electrokinetically transported from the SPE chamber into the main electrophoretic channel for further treatment and analysis.

Cell separations employing microfluidic devices and methods provide a cost-effective alternative to conventional flow cytometry techniques. In addition, when combined with biomagnetic separation technology, microfluidic approaches enable cell enrichment and detection that yield increased sensitivity and reduced background noise. Microfluidic-based magnetic isolation methods subject the target substances to minimal stress, and can accordingly leave cells intact and viable, ready for direct use in reverse transcription coupled with polymerase chain reaction amplification (RT-PCR). Microfluidic-based methods employ no phenol extractions, ethanol precipitations, or centrifugations, and employ few toxic reagents. Separations are provided without the use of expensive equipment and are highly scalable.

Example 5

Tools for Cost Effective Disease Management

As gene therapies move from the bench to the bedside, therapeutics and diagnostics will become more intimately interlinked. Consequently, monitoring the efficacy of DNA-based pharmaceuticals using bioinstruments at the bedside will become crucial to insuring the success of these treatments. More specifically, a microfluidic-based device for integrating cell collection and isolation processes with emerging molecular methods for DNA amplification and detection hold great promise for addressing this market need. Thus by combining methods as described in this application (particularly examples 3 and 4), it is possible to have in one analytical instrument the capability of cost-efficient disease prognosis and monitoring for helping the physician evaluate the appropriateness of a given genetic therapy. Such effective disease management strategies, in addition to other pharmacogenetic approaches, have the potential for widespread use as the post-genomic era rapidly approaches.

For the purpose of illustrating this embodiment of the invention, a system for managing blood-based diseases will be presented.

For background purposes, inherited blood disorders are the most common genetic diseases affecting humans. The World Health Organization estimates that about 5% of the world's population are carriers of different types of hemoglobin disorders and that about 300,000 new cases are diagnosed each year. Sickle cell anemia and, β-thallasemia are the two most common hemoglobinopathies that may be treated using gene therapies.

Of particular interest in treating the hemoglobinopathies, as well as monitoring the progress of their treatment, is the collection and isolation of hematopoietic stem cells. Employing the microfluidic device as shown in FIG. 22, when combined with the use of Dynal reagents for human hematopoietic progenitor cell selection as described in Example 4, a rapid and simple-to-use method for achieving the desired stem cell isolation is possible. For example, 1 ml of Dynabeads M-450 CD34 will isolate approximately $8 \times 10^7$ cells. 100 μl (one unit) of DETACHaBEAD CD34 is used to detach $4 \times 10^7$ (100 μl) Dynabeads M-450 CD34. Cells isolated with this Progenitor Cell Selection System are pure (95% from bone marrow, 90% from peripheral and cord blood) and phenotypically unaltered. On the same device, DNA analysis, including gene expression monitoring, is possible employing molecular genetic methods once the stem cells are isolated and then lysed. Thus, microfluidic-based bioanalytical devices and methods, as described in this embodiment of the invention, should prove to be invaluable tools for disease management at this emerging molecular medicine and diagnostics interface.

Example 6

Solid-phase Isolation and Enrichment

Solid phase extraction (SP) of a particular target from a heterogeneous mixture is achieved in the following embodiment of the invention by employing the selective surface properties of target-specific microparticles and mechanical means for retention of the beads within the SP chamber. Although biomagnetic separation methods are currently attractive because commercial reagents are readily available for a wide variety of bioresearch applications, other non-magnetic microfluidic-based approaches are possible for achieving comparable separations. In similar embodiments to those provided above, solid phase enrichment in a microfluidic format is presented. Beads with target-specific binding moieties can be retained within the enrichment chamber utilizing mechanical means, including filtration membranes or mesh screens. In addition, an agarose gel may be injected (from the waste reservoir 391 prior to the experiment) into channel 384 at the outlet of the enrichment chamber 380 to prevent the beads from escaping, yet allowing the wash and elusion buffers to pass through the highly porous media. Thus, each of the embodiments described in Example 2 for target isolation and purification from complex mixtures may be achieved, at least conceptually, without requiring the use of magnetic fields.

It is evident from the above results and discussion that convenient, integrated microchannel electrophoretic devices are disclosed which provide for significant advantages over currently available CE and MCE devices. Because the subject devices comprise microchannels as electrophoretic flowpaths, they provide for all of the benefits of CE and MCE devices, including rapid run times, the ability to use small sample volumes, high separation efficiency, and the like. Since the subject integrated devices comprise an enrichment channel, they can be employed for the analysis of complex sample matrices comprising analyte concentrations in the femtomolar to nanomolar range. However, because of the particular positional relationship of the enrichment channel and the main electrophoretic flowpath, the shortcomings of on-line configurations, such as band broadening and the like, do not occur in the subject devices. As the subject devices are integrated and compact, they are easy to handle and can be readily used with automated devices. Finally, with the appropriate selection of materials, the devices can be fabricated so as to be disposable. Because of their versatility and the sensitivity they provide, the subject devices are suitable for use in a wide variety of applications, including clinical electrophoretic assays.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An integrated microfluidic device comprising microchannels formed in a generally planar substrate, said device comprising:

an enrichment microchannel comprising an enrichment channel portion containing an enrichment medium, said enrichment channel portion having a sample inlet, a discharge outlet, an elution inlet, and an enriched fraction fluid outlet;

a main electrophoretic microchannel enclosing a main electrophoretic flowpath, said main electrophoretic microchannel being connected in fluid-conducting relationship to said enriched fraction fluid outlet, and said main electrophoretic microchannel comprising a detection region; and means for moving a sample into said enrichment channel portion by way of said sample inlet and out from said enrichment channel portion by way of said discharge outlet, whereby at least a fraction of a component of interest in the sample is retained by said enrichment medium;

means for moving at least a portion of the fraction of the component of interest out from said enrichment channel portion by way of said enriched fraction outlet and into said main electrophoretic microchannel, wherein said means for moving the fraction of the component of interest out from said enrichment channel portion and into said main electrophoretic microchannel comprises a first electrode located in said enrichment channel at a point upstream from said elution inlet and a second electrode located downstream from said detection region.

2. The device according to claim 1, further comprising a secondary microchannel connected in fluid-conducting relation between said enrichment fraction fluid outlet and said main electrophoretic microchannel.

3. The device according to claim 2 wherein said secondary microchannel encloses a secondary electrophoretic flowpath.

4. The device according to claim 2 wherein said secondary microchannel and said main electrophoretic microchannel intersect to form an injection cross.

5. An integrated microfluidic device comprising microchannels formed in a generally planar substrate, said device comprising:

an enrichment microchannel comprising an enrichment channel portion containing an enrichment medium, said enrichment channel portion having a first inlet and a first fluid outlet;

a main electrophoretic microchannel enclosing a main electrophoretic flowpath, said main electrophoretic microchannel being connected in fluid-conducting relation to said first fluid outlet, and said main electrophoretic microchannel comprising a detection region;

means for moving a sample into said enrichment channel portion by way of said first inlet and out from said enrichment channel portion by way of said first fluid outlet, whereby at least a fraction of a component of interest in the sample is retained by said enrichment medium;

a discharge channel connected in fluid communication with said first fluid outlet at a point upstream from said main electrophoretic flowpath, for discharging a portion of said sample other than said fraction of the component of interest from said main electrophoretic flowpath; and means for moving at least a portion of the fraction of the component of interest from said enrichment channel portion by way of said first fluid outlet and into said main electrophoretic microchannel, wherein said means for moving at least a portion of the fraction of the component of interest out from said enrichment channel portion by way of said first fluid outlet and into said main electrophoretic microchannel comprises a first electrode located in said enrichment channel upstream of said first inlet and a second electrode located downstream from said detection region.

6. The device according to claim 5, further comprising a secondary microchannel connected in fluid conducting relation between said first fluid outlet and said main electrophoretic microchannel.

7. The device according to claim 6 wherein said secondary microchannel and said main electrophoretic microchannel intersect to form an injection cross.

8. An integrated microfluidic device comprising microchannels formed in a generally planar substrate, said device comprising:

an enrichment microchannel comprising an enrichment channel portion containing an enrichment medium, said enrichment channel portion having a first inlet a first fluid outlet;

a main electrophoretic microchannel enclosing a main electrophoretic flowpath, said main electrophoretic microchannel being connected in fluid-conducting relation to said first outlet, and said main electrophoretic microchannel comprising a detection region;

means for moving a sample into said enrichment channel portion by way of said first inlet and out from said enrichment channel portion by way of said first fluid outlet, whereby at least a fraction of a component of interest in the sample is retained by the enrichment medium;

a discharge channel connected in fluid communication with said first fluid outlet at a point upstream from said main electrophoretic flowpath, for discharging a portion of said sample other than said fraction of the component of interest away from said main electrophoretic flowpath;

means for moving at least a portion of the fraction of the component of interest out from said enrichment channel portion by way of said first fluid outlet and into said main electrophoretic microchannel, wherein said means for moving at least a portion of the fraction of the component of interest out from said enrichment channel portion by way of said first fluid outlet and into said main electrophoretic microchannel comprises a first electrode located upstream from said first inlet and a second electrode located downstream from said detection region; and a plurality of input microchannels connected in fluid relation to said first fluid inlet, said plurality of input microchannels comprising at least a sample input microchannel an an elution input microchannel.

9. A microfluidic device for use with a detector to analyze a sample having an analyte portion and a waste portion, the microfluidic device comprising a substrate having a surface and comprising at least one microchannel, an inlet in fluid communication with said microchannel proximal to a first end of said microchannel, and a waste outlet, enrichment means in said microchannel for separating at least a part of the analyte portion from the waste portion, said microchannel having a detection region downstream of the enrichment means accessible by the detector for analyzing a characteristic of the sample, said waste outlet in fluid communication with said microchannel upstream of the detection region and adjacent said enrichment means, transfer means for moving the sample from the inlet to the enrichment means and the waste portion from the enrichment means to the waste outlet and at least first and second spaced-apart electrodes, with one of said electrodes proximal to said inlet and in electrical contact with the sample when the sample is present in the microfluidic device and the other of said electrodes is downstream from said detection region for moving the analyte portion from the enrichment means to the detection means whereby part of the analyte portion but not the waste portion is moved to the detection region for facilitating accurate analysis by the detector of said part of the analyte portion at the detection region.

10. The microfluidic device according to claim 9 wherein the enrichment means includes a chromatographic material.

11. The microfluidic device according to claim 9 wherein the enrichment means includes an electrophoretic gel medium.

12. The microfluidic device according to claim 9 wherein the substrate is provided with an additional inlet in fluid communication with the at least one microchannel upstream of the enrichment means, means for introducing a solution into the additional inlet to contact the enrichment means and separate said part of the analyte portion from the enrichment means.

13. The microfluidic device according to claim 9 wherein the waste outlet is in fluid communication with the at least one microchannel at the enrichment means so that the waste portion exits the at least one microchannel at the enrichment means.

14. The microfluidic device according to claim 9 wherein the at least one microchannel includes a first microchannel portion extending from the inlet to the waste outlet and a second microchannel portion which meets the first microchannel portion at an intersection and extends to the detection region, the enrichment means being at least partially in the intersection.

15. The microfluidic device according to claim 9 wherein the waste outlet is in fluid communication with the at least one microchannel between the enrichment means and the detection region.

16. The microfluidic device according to claim 9 further comprising an electrophoretic medium disposed in the at least one microchannel in the vicinity of the detection region, the waste outlet being in fluid communication with the at least one microchannel between the enrichment means and the electrophoretic medium.

17. The microfluidic device according to claim 9 wherein the transfer means includes a third electrode in electrical contact with the waste portion when the waste portion is in said waste outlet.

18. The microfluidic device according to claim 9 wherein the at least one microchannel includes a first microchannel portion downstream from the enrichment means and a second microchannel portion which meets the first microchannel portion at an intersection and extends to the detection region, the at least first and second spaced-apart electrodes including first and second spaced-apart electrodes for moving said part of the analyte portion from the enrichment means through the first microchannel portion to the intersection and third and fourth spaced-apart electrodes for moving said part of the analyte portion from the intersection through the second microchannel portion to the detection region.

19. The microfluidic device according to claim 9 wherein the substrate is provided with an additional inlet in fluid communication with the at lest one microchannel and wherein the at least one microchannel includes a first microchannel portion extending from the inlet to the enrichment means, a second microchannel portion extending from the additional inlet to intersect the first microchannel portion whereby a fluid other than the sample can be supplied to the at least one microchannel by the additional inlet.

20. The microfluidic device according to claim 9 wherein the substrate is provided with a plurality of additional inlets in fluid communication with the at least one microchannel and wherein the at least one microchannel includes a first microchannel portion extending from the inlet to the enrichment means, a plurality of additional microchannel portions extending from the additional inlets to intersect the first microchannel portion whereby a plurality of fluids other than the sample can be supplied to the at least one microchannel by the additional inlets.

21. The microfluidic device according to claim 9, wherein said microchannel comprises an additional detection region, downstream from said waste outlet.

22. The microfluidic device according to claim 21 wherein the analyte portion includes a plurality of different fractions of interest, the device further comprising an additional enrichment means in said microchannel between said enrichment means and said inlet, said additional enrichment means enhancing a different fraction of interest in the analyte portion.

23. The microfluidic device according to claim 22 wherein the analyte portion includes a plurality of different nucleic acid fragments and wherein the additional enrichment means each includes a molecular probe for capturing one of the different nucleic acid fragments.

24. The microfluidic device according to claim 21, wherein the two detection regions are disposed in series along said microchannel.

25. The microfluidic device according to claim 21, wherein the two detection regions are disposed in parallel along said microchannel.

26. The microfluidic device according to claim 25 wherein said microchannel is connected to a branch microchannel, said branch microchannel comprising two detection regions.

27. The microfluidic device according to claim 25 wherein the at least one microchannel includes a first microchannel portion and a plurality of second microchannel portions which meet the first microchannel portion at respective intersections spaced-apart along the first microchannel portion, one of the first-named and additional detection regions being in each of the plurality of second microchannel portions.

28. The microfluidic device according to claim 27 wherein the at least first and second spaced-apart electrodes includes first and second spaced-apart electrodes for each of the second microchannel portions to move said part of the analyte portion through the respective first-named or additional detection region.

29. A device according to claim 9 for use with a sample having first and second analyte portions wherein said microchannel includes a branched microchannel portion having first and second branch microchannel portions, said inlet being upstream of the branched microchannel portion, second enrichment means being in said first branch microchannel portion for separating at least part of the first analyte portion from the second analyte portion, said first branch microchannel portion comprising a second detection region downstream from said second enrichment means and in fluid communication with a waste outlet downstream of and proximal to said enrichment means, the first and second spaced-apart electrodes positioned for moving said part of the first analyte portion from the enrichment means to the detection region.

30. The microfluidic device according to claim 29 wherein each of the first and second branch microchannel portions includes a first microchannel segment downstream from the respective enrichment means and a second microchannel segment which meets the first microchannel segment at an intersection and extends to the respective detection region, the at least first and second spaced-apart electrodes including first and second spaced-apart electrodes for moving said part of the first analyte portion from the first-named enrichment means through the first microchannel segment to the intersection and at least a first additional electrode for moving said part of the first analyte portion from the intersection through the second segment portion to the first-named detection region and the at least a third electrode including at least a third electrode for moving said part of the second analyte portion from the additional enrichment means through the first microchannel segment to the intersection and at least a second additional electrode for moving said part of the second analyte portion from the intersection through the second segment portion to the additional detection region.

31. The microfluidic device according to claim 9 wherein the enrichment means includes affinity binding capture and release molecules to capture at least a part of the analyte portion so as to separate at least a part of the analyte portion from the waste portion.

32. The microfluidic device according to claim 31 wherein the affinity binding capture and release molecules are bound to a plurality of bodies capable of producing a magnetic field.

33. The microfluidic device according to claim 32 further comprising a magnet for coupling magnetically to at least some of the bodies capable of producing a magnetic field.

34. A microfluidic device for use with first and second detectors to analyze a first analyte portion and a second analyte portion in a sample, said microfluidic device comprising a substrate having a surface and being provided with a microchannel network formed therein, the microchannel network comprising a main microchannel including a branched microchannel portion connected to first and second branch microchannel portions, first enrichment means in the first branch microchannel portion for separating at least part of the first analyte portion from the second analyte portion, second enrichment means in the second branch microchannel portion for separating at least part of the second analyte portion from the first analyte portion, the first branch microchannel portion having a first detection region downstream of the first enrichment means accessible by the first detector for analyzing a characteristic of the first analyte portion, the second microchannel portion having a second detection region downstream of the second enrichment means accessible by the second detector for analyzing a characteristic of the second analyte portion, first and second spaced-apart electrodes in electrical contact with an electrophoretic medium in said microchannel network for moving said part of the first analyte portion from the first enrichment means to the first detection region and at least a third electrode in electrical contact with the electrophoretic medium for moving the second analyte portion from the second enrichment means to the second detection region whereby the first analyte portion can be analyzed by the first detector at the first detection region and the second analyte portion can be analyzed by the second detector at the second detection region.

35. The microfluidic device according to claim 34 wherein the substrate has a first waste outlet in fluid communication with the first branch microchannel portion upstream of the first detection region for removing the second analyte portion from the first branch microchannel portion so as not to contaminate the first detection region with the second analyte portion and wherein the substrate has a second waste outlet in fluid communication with the second branch microchannel portion upstream of the second detection region for removing the first analyte portion from the second branch microchannel portion so as not to contaminate the second detection region with the first analyte portion.

36. The microfluidic device according to claim 35 wherein the substrate is provided with an outlet reservoir in fluid communication with the first and second waste outlets.

* * * * *